US012390555B2

(12) United States Patent
Atlas et al.

(10) Patent No.: US 12,390,555 B2
(45) Date of Patent: Aug. 19, 2025

(54) SILK FIBROIN BIOCOMPATIBLE POLYURETHANE MEMBRANES

(71) Applicant: Ear Science Institute Australia Incorporated, Subiaco (AU)

(72) Inventors: Marcus Atlas, Subiaco (AU); Benjamin Allardyce, Ocean Grove (AU); Rodney Dilley, City Beach (AU); Rangam Rajkhowa, Grovedale (AU)

(73) Assignee: Ear Science Institute Australia Incorporated, Subiaco (AU)

( * ) Notice: Subject to any disclaimer, the term of this patent is extended or adjusted under 35 U.S.C. 154(b) by 0 days.

(21) Appl. No.: 18/316,360

(22) Filed: May 12, 2023

(65) Prior Publication Data

US 2023/0355839 A1 Nov. 9, 2023

Related U.S. Application Data

(63) Continuation of application No. 16/089,243, filed as application No. PCT/AU2017/050335 on Apr. 13, 2017, now Pat. No. 11,684,695.

(30) Foreign Application Priority Data

Apr. 14, 2016 (AU) .................... 2016901399

(51) Int. Cl.
| | | |
|---|---|---|
| A61L 27/22 | (2006.01) | |
| A61F 2/18 | (2006.01) | |
| A61L 27/26 | (2006.01) | |
| A61L 27/36 | (2006.01) | |
| A61L 27/44 | (2006.01) | |
| A61L 27/54 | (2006.01) | |
| C08L 75/04 | (2006.01) | |
| C08L 89/04 | (2006.01) | |

(52) U.S. Cl.
CPC ............ *A61L 27/3604* (2013.01); *A61F 2/18* (2013.01); *A61L 27/225* (2013.01); *A61L 27/26* (2013.01); *A61L 27/44* (2013.01); *A61L 27/54* (2013.01); *C08L 75/04* (2013.01); *C08L 89/04* (2013.01); *A61F 2002/183* (2013.01); *A61L 2300/40* (2013.01); *A61L 2430/14* (2013.01)

(58) Field of Classification Search
None
See application file for complete search history.

(56) References Cited

U.S. PATENT DOCUMENTS

| | | | | |
|---|---|---|---|---|
| 2004/0005363 A1* | 1/2004 | Tsukada | ................ | A61L 27/227 106/156.5 |
| 2010/0068517 A1* | 3/2010 | Liu | ......................... | D01B 7/00 428/401 |
| 2010/0286774 A1 | 11/2010 | Kweon et al. | | |
| 2011/0111031 A1* | 5/2011 | Jiang | .................... | A61K 9/0024 514/327 |
| 2014/0303727 A1 | 10/2014 | Atlas et al. | | |
| 2015/0283298 A1* | 10/2015 | Kaplan | .................. | A61L 27/56 264/43 |

FOREIGN PATENT DOCUMENTS

| | | | | |
|---|---|---|---|---|
| KR | 20070000892 A | * | 1/2007 | |
| WO | WO-9515156 A1 | * | 6/1995 | ............ A01N 25/34 |
| WO | 2005052019 A1 | | 6/2005 | |
| WO | 2013006908 A1 | | 1/2013 | |
| WO | WO-2014066884 A1 | * | 5/2014 | ............ A61L 27/12 |

OTHER PUBLICATIONS

Um et al., Structural characteristics and properties of the regenerated silk fibroin prepared from formic acid, International Journal of Biological Macromolecules 29 (2001) 91-97 (Year: 2001).*
Zhang et al., Silk Fibroin Based Porous Materials, Materials 2009, 2, 2276-2295; doi:10.3390/ma2042276 (Year: 2009).*
Machine Translation of WO 95/15156 (Year: 1995).*
Machine Translation of KR-20070000892-A (Year: 2007).*
Bai, et al., "Fabrication and Characterization of Silk Fibroin Powder/Polyurethane Fibrous Membrane", Polymer Engineering and Science, 2012, pp. 2025-2032.
Chiarini, et al., "Silk fibroin/poly(carbonate)-urethane as a substrate for cell growth: in vitro interactions with human cells", Biomaterials, 24, 2003, pp. 789-799.
Dal Pra, et al., "Silk Fibroin-Coated Three-Dimensional Polyurethane Scaffolds for Tissue Engineering: Interactions with Normal Human Fibroblasts", Tissue Engineering, vol. 9, No. 6, 2003, pp. 1113-1121.
Luo, et al., "A one-pot preparation of silk fibroin modified with polyurethane micro-particles", New J. Chem., 37, 2013, pp. 3109-3115.
Park, et al., "Silk fibroin-polyurethane blends: Physical properties and effect of silk fibroin content on viscoelasticity, biocompatibility and myoblast differentiation", Acta Biomaterialia, 9, 2013, pp. 8962-8971.
Petrini, et al., "Silk Fibroin-polyurethane scaffolds for tissue engineering", Journal of Materials Science: Materials in Medicine, 12, 2001, pp. 849-853.
Tao, et al., "Structure and properties of composites compression-molded from silk fibroin powder and waterborne polyurethane", Polymers Advanced Technology, 23, 2012, pp. 639-644.
Yang, et al., "Inflammatory response of native silk fibroin powder/polyurethane composite membrane containing aspirin in vivo", Advanced Materials Research, vols. 175-176, 2011, pp. 236-241.
International Search Report issued May 16, 2017 for International Patent Application No. PCT/AU2017/050335, 5 pages.

(Continued)

*Primary Examiner* — Jennifer A Berrios
(74) *Attorney, Agent, or Firm* — Kagan Binder, PLLC

(57) ABSTRACT

The present invention relates to the preparation of a membrane for use in the repair of the middle ear including perforations and damage to the tympanic membrane. More particularly, the invention provides for compositions and methods for preparing silk fibroin biocompatible polyurethane membranes using a solvent, which have improved biodegradation, mechanical and vibroacoustic properties.

5 Claims, 3 Drawing Sheets

(56) References Cited

OTHER PUBLICATIONS

Stefanovic et al., Poly(urethane-dimethylsiloxane) copolymers displaying a range of soft segment contents, noncytotoxic chemistry, and nonadherent properties toward endothelial cells: Poly(Urethane-Dimethylsiloxane) Copolymers, Journal of Biomedical Materials Research Part A 103(4), Apr. 2015, pp. 1459-1475.
Liu et al., Controlled release of heparin from blended polyurethane and silk fibroin film, Materials Letters 63(2), 2009, pp. 263-265.

* cited by examiner

SILK FIBROIN BIOCOMPATIBLE POLYURETHANE MEMBRANES

CROSS REFERENCE TO RELATED APPLICATIONS

This application is a Continuation of U.S. application Ser. No. 16/089,243, filed on Sep. 27, 2018, which claims priority to International Application No. PCT/AU2017/050335, filed on Apr. 13, 2017, which claims the benefit of Australian Application No. AU 2016901399, filed Apr. 14, 2016, which are each incorporated herein by reference in their entireties.

FIELD OF THE INVENTION

The present invention relates to the preparation of a membrane for use in the repair of the middle ear including perforations and damage to the tympanic membrane. More particularly, the invention provides for compositions and methods for preparing silk fibroin biocompatible polyurethane membranes using a solvent, which have improved biodegradation, mechanical and vibroacoustic properties.

BACKGROUND

The following discussion is intended to facilitate an understanding of the present invention only. The discussion is not an acknowledgement or admission that any of the material referred to is or was part of the common general knowledge as at the priority date of the application.

Chronic perforations of the eardrum or tympanic membrane are relatively common conditions which require surgical intervention with a graft material to cover the perforation, a technique known as myringoplasty or tympanoplasty type 1.

Autografts such as muscle fascia, fat, perichondrium and cartilage are the most common tissues used in this surgery. However, this approach has various limitations, including mismatch of graft mechanical properties with the tympanic membrane, non-transparency of grafts, donor site morbidity, and increased operation time.

With developments in materials science over recent years, various alternative scaffold materials, such as decellularized tissue (e.g. AlloDerm®), polymers (e.g. hyaluronic acid, chitosan and calcium alginate) and synthetic materials [e.g. poly(glycerol sebacate) (PGS)], have been investigated as grafting materials. However, the choice of an optimal scaffold remains unresolved.

Silk fibroin has been extensively researched for its potential as a bioscaffold in tissue engineering. It is derived from silkworm cocoons following the removal of the antigenic protein sericin. Silk fibroin solutions can be processed into various forms such as films, fibers, mats, hydrogels and sponges, catering for broad biomedical applications.

Silk fibroin is biodegradable, biocompatible, and has superior mechanical strength and toughness compared to most other natural and synthetic biomaterials such as collagen and polylactic acid (PLA). Importantly, silk fibroin can support the attachment and growth of many different cell types such as chondrocytes, endothelium, epithelium, glia, fibroblasts, osteoblasts and keratinocytes.

One of the major advantages of silk is the ability to alter important properties to suit a particular tissue engineering application through simple change of processing conditions. Manipulation of processing methods (e.g. water vs organic solvent, water vs alcohol annealing) and processing variables (e.g. drying rate, silk concentrations) can alter the physical and structural properties of silk and affect its performance as a scaffold material.

In many cases, however, adding a blending component to affect mechanical properties remains a challenge. In particular, avoiding additions of other polymers while generating membranes that maintain stability for extended time frames remains a goal.

There remains a need to modify the physical and mechanical properties of silk fibroin films to improve mechanical and vibroacoustic properties and provide for more flexible silk fibroin-based systems for biomedical and other applications.

SUMMARY OF THE INVENTION

The inventors have identified a principal of general application in that they have identified that by using an appropriate solvent and by including a matrix agent such as a biocompatible polyurethane it is possible to alter the mechanical and vibroacoustic characteristics, enzymatic degradation rate and strength and flexibility of a silk fibroin membrane.

Lyophilized silk can be stored for long periods. This allows films to be cast as required, whereas aqueous silk fibroin solution must be cast immediately and used within a few days to weeks before the solution gels and becomes unusable. Moreover, devices made with a matrix agent like a biocompatible polyurethane silk are not soluble in water, dependent upon the solvent used, and do not require annealing with ethanol or methanol, a step which may cause the film to shrink and distort.

In a first aspect, the invention provides a silk fibroin/biocompatible polyurethane membrane matrix, wherein the membrane matrix:
 (a) includes silk fibroin in an amount ranging from about 0.1% to about 95% of the total volume of the membrane (w/w);
 (b) includes at least 1% (w/w) biocompatible polyurethane;
 (c) transmits sound waves between 20 Hz and 20 KHz to the middle ear in vivo;
 (d) has a tensile strength between 5 MPa to 100 MPa; and
 (e) is fabricated from biocompatible polyurethane and silk protein solubilized in a solvent compatible with both the biocompatible polyurethane and the silk fibroin.

The silk fibroin membrane matrix of the invention provides a construct for tissue engineering. It provides a matrix upon which keratinocytes, fibroblasts, mucosal epithelium, endothelial cells, chondrocytes etc. may grow. The membrane matrix may also be used in cell therapies using induced pluripotent stem cells, adult stem cells and embryonic stem cells, and combinations thereof to provide a scaffold upon which these cells can grow in a patient.

The silk fibroin membrane matrices of the invention have distinct properties compared with silk fibroin films lacking biocompatible polyurethane. Elasticity and durability are enhanced with the use or inclusion and use of biocompatible polyurethane. The use of biocompatible polyurethane in combination with silk fibroin in materials processing also expands the functional features attainable with silk fibroin, and the formation of more flexible films with potential utility in biomaterial and device.

In a second aspect, the invention provides a silk fibroin/biocompatible polyurethane membrane matrix, wherein the membrane matrix:

(a) includes silk fibroin in an amount ranging from about 0.1% to about 95% of the total volume of the membrane (w/w);
(b) includes at least 1% (w/w) biocompatible polyurethane;
(c) transmits sound waves between 20 Hz and 20 KHz to the middle ear in vivo;
(d) has a tensile strength between 5 MPa to 100 MPa; and
(e) is fabricated as a composite membrane where the silk fibroin provides a coating to a biocompatible polyurethane membrane.

In a third aspect, the invention provides a method of fabricating a silk fibroin biocompatible polyurethane membrane matrix comprising the steps of:
(a) preparing silk protein or a silk protein complex solution after removal of sericin from a cocoon or fibre;
(b) dissolving biocompatible polyurethane and silk fibroin using a suitable solvent; and
(c) drying the prepared solution to fabricate a silk protein and polyurethane membrane matrix.

In a fourth aspect, the invention provides a device for the repair of tympanic membrane perforations, and particularly a chronic perforation comprising a membrane matrix as described herein. In this respect, the membrane matrix preferably has a tensile strength between approximately 10 MPa to 95 MPa, and more preferably, a tensile strength between approximately 10 and approximately 50 MPa.

In one embodiment, provided herein is a silk fibroin biocompatible polyurethane membrane matrix, wherein the membrane matrix is resistant to degradation and/or provides long term structural support to resist retraction, atelectasis and cholesteatoma.

In one embodiment of this aspect, the device comprises a plurality of silk fibroin biocompatible polyurethane membrane matrices. In this embodiment, the device may comprise at least one first membrane matrix comprising silk fibroin and at least one second membrane matrix comprising a biocompatible polyurethane.

In a fifth aspect, the invention provides a device for use in the repair of the ear canal, the pars flaccida and/or the scutum bone comprising a membrane matrix as described herein.

In a sixth aspect, the invention resides in the use of a membrane matrix, as herein described, to support proliferation, migration and/or adhesion of at least the cells of an ear drum when grafted or applied to the ear drum of a subject, or more preferably, the tympanic membrane such as a perforated tympanic membrane of a subject, and/or the pars flaccida and/or the scutum bone proximal to the pars flaccida of a subject. The invention also provides for the use of a membrane matrix as herein described in mastoid obliteration techniques for reconstruction of an ear canal of a subject after tympanomastoidectomy, including to cover a hydroxyapatite free graft.

In a further aspect, the invention provides a method for repairing the ear drum, and more preferably a tympanic membrane perforation such as a chronic tympanic membrane perforation, and/or a defective pars flaccida and/or the scutum bone proximal to the pars flaccida, in a subject in need of such treatment, said method comprising a membrane matrix, as herein described to the damaged tissue or tissue to be repaired.

The silk fibroin biocompatible polyurethane membrane matrix produced according to the invention may include at least one active agent. The active agent is preferably selected from the group consisting of: cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, drugs, and combinations thereof.

The present invention provides for membrane matrices comprising silk fibroin and biocompatible polyurethane, which have distinct properties compared with silk fibroin membranes lacking biocompatible polyurethane. More specifically, altering solubility, biocompatibility, strength, degradation characteristics and flexibility with the use or inclusion and use of biocompatible polyurethane.

The use of biocompatible polyurethane in combination with silk fibroin in materials processing expands the functional features attainable with silk fibroin, and the formation of stronger or more flexible films with potential utility in biomaterial and device applications.

The invention also provides a kit for use in the repair of an ear canal, a tympanic membrane perforation, and/or the pars flaccida of a subject, said kit comprising a membrane matrix, as herein described. The kit may also comprise one or more solutions of any of the bioactive molecules, as herein described. The one or more solutions of bioactive molecules may be for application to the membrane prior to implantation of the membrane matrix into a subject, or for application to the membrane matrix following implantation or grafting of the membrane matrix to the subject which may occur once, or on multiple occasions thereafter.

Thus, the membrane matrix of the present invention provides a customized graft implant for use in the repair and regeneration of damaged tissue. In one form that damaged tissue is a perforated tympanic membrane and/or the reconstruction and regeneration of the ear canal including the pars flaccida and scutum bone in a subject in need of such treatment.

Customization of the membrane matrix can assist in facilitating regeneration to substantially resemble the native form of the tissue it is being used to repair thereby enabling better opportunity for improved healing outcomes for a subject.

BRIEF DESCRIPTION OF THE DRAWINGS

These and/or other aspects and advantages of the invention will become apparent and more readily appreciated from the following description of the exemplary embodiments, taken in conjunction with the accompanying figures.

In the figures the following abbreviations apply:
TPU Thermoplastic polyurethane
PBS Phosphate buffered saline

DETAILED EMBODIMENTS OF THE INVENTION

Figure 1A:
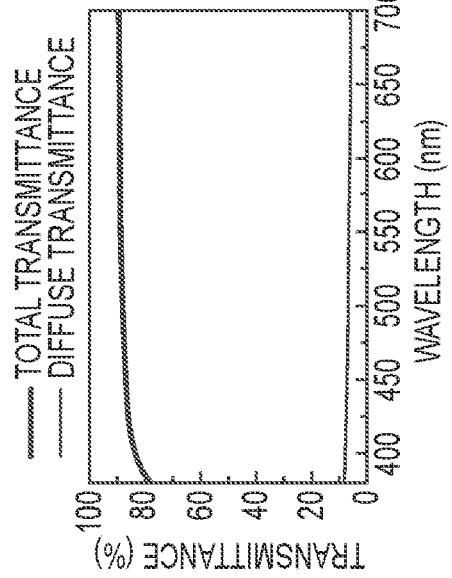
FIG. 1A is a plot showing the transparency of pure silk membranes as a function of wavelength

The inventors have discovered that by using an using an appropriate solvent and by including a matrix agent such as a biocompatible polyurethane it is possible to alter the mechanical properties, enzymatic degradation rate and flexibility of a silk fibroin membrane. Accordingly, the present invention is directed to composite silk fibroin membranes that are prepared in combination with a biocompatible polyurethane. That matrix (i) can be stored for relatively long periods, (ii) are relatively insoluble in water, (iii) have, biocompatible, and an lower elasticity compared to many other natural and silk fibroin synthetic biomaterials.

Silk fibroin membrane matrixes produced according to the invention have multiple uses such as in scaffolds in tissue engineering as films, fibres, mats, hydrogels and sponges, catering for broad biomedical applications.

When the silk fibroin membrane matrixes are used in the repair of tympanic membranes, the inventors have discovered that by using a biocompatible polyurethane it is possible to at least improve one or more of the mechanical and vibroacoustic characteristics of a silk fibroin membrane.

For convenience, the following sections generally outline the various meanings of the terms used herein. Following this discussion, general aspects regarding silk fibroin membrane matrices are discussed, followed by specific examples demonstrating the properties of various embodiments of the membranes and how they can be employed.

Definitions

Those skilled in the art will appreciate that the invention described herein is susceptible to variations and modifications other than those specifically described. The invention includes all such variations and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness. None of the cited material or the information contained in that material should, however be understood to be common general knowledge.

Manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc.). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Reference to cited material or information contained in the text should not be understood as a concession that the material or information was part of the common general knowledge or was known in Australia or any other country.

For the purposes of describing the device of the invention and how it may be used, the term "perforated", "perforation" or any other variation of "perforate" thereof will be understood to include any damage to the tympanic membrane of a subject that can be repaired using the device of the invention. In some non-exhaustive examples, such damage may include a hole or tear in the tympanic membrane or a deformity or loss of any part of the membrane or a layer of a membrane as a result of physical forces or disease. The tympanic membrane or eardrum comprises the pars tensa, and pars flaccida in the medial border of the ear canal. The pars flaccida is subject to retraction and cholesteatoma, and the adjacent tympanic cavity attic, scutum bone and soft tissue of the ear canal often require reconstruction after surgical treatment of this condition.

For the purposes of describing the device of the invention and how it may be used, the term "defective" or any other such variation of the term thereof will be understood to include any damage or disease to the soft tissue of the pars flaccida or bone of the surrounding area of a subject, that can be repaired or reconstructed using the device of the invention. This may include, damage or disease from cholesteatoma, or necessary repair of an ear canal of a subject following mastoidectomy, amongst others.

For the purposes of describing the device of the invention, the term "biocompatible polyurethane" will be understood to mean a polymer composed of organic units joined by carbamate (urethane) links which, when implanted in the body, does not cause any significant deleterious changes to the surrounding tissue. Biocompatible polyurethanes have the ability to perform the desired medical therapy, without eliciting any undesirable local or systemic effects in the recipient or beneficiary of that therapy. Biocompatible polyurethanes do not have any toxic or injurious effects on biological systems.

Features of the invention will now be discussed with reference to the following non-limiting description and examples.

EMBODIMENTS

Silk fibroin membrane matrixes produced according to the invention are biodegradable, biocompatible, and are improved in one or more of their mechanical strength, elongation and stiffness compared to most other natural and synthetic biomaterials such as collagen and polylactic acid (PLA).

A. Silk Fibroin Membrane Matrix

The present invention provides for a silk fibroin biocompatible polyurethane membrane matrix. Membrane matrixes of the invention exhibit higher ductility than silk films lacking biocompatible polyurethane.

Membranes of the invention are fabricated for repair of tympanic membrane perforations, in particular a chronic perforation. In addition, or in the alternative, membranes of the invention may be fabricated for repair of the ear canal, in particular the pars flaccida and/or the scutum bone of the subject. Preferably, the membrane is fabricated to deliver a device suitable, inter alia, for repair of a tympanic membrane.

In a first aspect the invention provides a silk fibroin/biocompatible polyurethane membrane matrix, wherein the membrane matrix:
(a) includes silk fibroin in an amount ranging from about 0.1% to about 95% of the total volume of the membrane (w/w);
(b) includes at least 1% (w/w) biocompatible polyurethane;
(c) transmits sound waves between 20 Hz and 20 KHz to the middle ear in vivo;
(d) has a tensile strength between 5 MPa to 100 MPa; and
(e) is fabricated from biocompatible polyurethane and silk protein solubilized in in a solvent capable of dissolving the biocompatible polyurethane without degrading the silk fibroin.

In a second aspect, the invention provides a silk fibroin/biocompatible polyurethane membrane, wherein the membrane:
(a) includes silk fibroin in an amount ranging from about 0.1% to about 95% of the total volume of the membrane (w/w);
(b) includes at least 1% (w/w) biocompatible polyurethane;
(c) transmits sound waves between 20 Hz and 20 KHz to the middle ear in vivo;
(d) has a tensile strength between 5 MPa to 100 MPa; and
(e) is fabricated as a composite membrane matrix where the silk fibroin provides a coating to a biocompatible polyurethane membrane.

Silk fibroin is present in the membrane in an amount ranging from about 0.1% to about 95% (wt %) of the total volume of the membrane. Preferably silk fibroin is present in an amount selected from about 5.0% to about 75.0%, of the total weight of the membrane. Desirably the silk fibroin content is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75% of the total weight of the membrane.

The biocompatible polyurethane used in the present invention is preferably composed of one or more polymers of organic units which, when implanted in the body, do not cause significant deleterious changes to the surrounding tissue. For example the biocompatible polyurethane can be composed of one or more polymers of organic units joined by carbamate (urethane) links.

The biocompatible polyurethanes used in the invention can be used in medical therapy, without eliciting undesirable local or systemic effects in the recipient. Preferably they will not have any toxic or injurious effects on biological systems. In a highly preferred embodiment the biocompatible polyurethane is a poly(alkylene oxide) oligomer and co-oligomer composite/preparation or a composite/covalently bound preparation including a biocompatible polyurethane containing a,x-dihydroxypropylpoly (dimethylsiloxane) (PDMS) (Examples of such a composition may be found in WO/1992/000338, WO/1992/009647, WO/1999/001496, WO/1999/003863, WO/1999/050327, WO/1998/013405, WO/2001/007499, WO/1998/054242, WO/2000/064971, and WO/2005/052019. The contents of each the identified specifications are specifically incorporated herein by reference. Other examples of PDMS biocompatible polyurethanes that may be used in the invention include Elast-Eon™ (based on PDMS/PHMO macrodiol) from AorTech Biomaterials Pty which is used in cardiovascular applications (vascular grafts, blood pumps, artificial heart, cardiac pacemakers, stent, etc.), catheters, orthopedic implants; Angioflex® [based on PDMS/poly(tetramethylene oxide) macrodiol] from Applied Biomedical Corp., which is used for heart valves, artificial heart blood pumping diaphragms; Cardiothane®-51 [based on PDMS/poly(tetramethyleneoxide) macrodiol] from Arrow International, used for artificial hearts, intra-aortic balloons and blood conduits; 1,11-14 PurSil™10,15 and PurSil-AL™ (aromatic and aliphatic siloxane polyether TPUs) from Polymer Technology Group are used in long- and short-term biomedical applications, respectively. Examples of PDMS polyurethane copolymers may be found in Stefanovic I. S., et al, (2015) JOURNAL OF BIOMEDICAL MATERIALS RESEARCH A, 103A(4), 1459-1475, the contents of which are specifically incorporated herein by reference. Yet another form of polyurethane that can be used in the method of the invention is selected from Pellethene 2368-80A (Dow Chemical Co) or and Biomer.

The biocompatible polyurethane content of the silk fibroin biocompatible polyurethane membrane will be at least about 1% (w/v). Preferably the biocompatible polyurethane content is selected from the group consisting of equal to or greater than: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99% of the total volume of the membrane (w/v).

In one embodiment, the content ratio of silk to biocompatible polyurethane in the membrane matrix is selected from the group consisting of: 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5; 1:10, 1:10.5, 1:11, 1:11.5, 1:12, 1:12.5, 1:13, 1:13.5, 1:14, 1:14.5, 1:15, 1:15.5, 1:16, 1:16.5, 1:17, 1:17.5, 1:18, 1:18.5, 1:19, 1:19.5, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99 and 1:100.

In one embodiment, the content ratio of biocompatible polyurethane to silk in the membrane matrix is selected from the group consisting of: 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5; 1:10, 1:10.5, 1:11, 1:11.5, 1:12, 1:12.5, 1:13, 1:13.5, 1:14, 1:14.5, 1:15, 1:15.5, 1:16, 1:16.5, 1:17, 1:17.5, 1:18, 1:18.5, 1:19, 1:19.5, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99 and 1:100.

The tensile strength of the membrane matrix can be varied by altering the content of the silk fibroin and the glycerol. Ideally, the tensile strength is selected for the purpose that the membranes are bioengineered for. For example, where the membranes are formed as a bioscaffold for tissue engineering, the tensile strength can be as great as 150 MPa or even greater, if required. Desirably, the tensile strength of the membrane matrix is in the range of 5 MPa and 100 MPa with tensile strengths of 9, 10, 11, 12, 13, 14, 15, 16, 17, 18, 19, 20, 30, 40, 50, 60, 70, 80, 90, 100, MPa or any value in between these numbers, being acceptable depending on the purpose for which the material is being utilised. For example, where the membrane matrix is used as a scaffold repair of bone or in wound repair the tensile strength of the device can be between 50 MPa and 150 MPa. Alternatively, where the membrane matrix is used as a device for repair of tympanic membranes the tensile strength of the material will be in the range of 5 to 50 MPa. For example, such a membrane matrix can have a tensile strength of 9, 10, 10.5, 11, 11.5, 12, 12.5, 13, 13.5, 14, 14.5, 15, 15.5, 16, 16.5, 17, 17.5, 18, 18.5, 19, 19.5, 20, 25, 30, 35, 40, 45, 50 MPa or any value in between these numbers.

In one embodiment, a single membrane matrix may be present. In an alternative embodiment, multiple layers of membrane matrices may be present.

In one embodiment of this aspect, the multiple layers of membrane matrices may comprise the same type of membrane matrix. In an alternate embodiment, the multiple layers of membrane matrices may comprise different types of membrane matrices.

For example, multiple layers of the silk fibroin biocompatible polyurethane may be used simultaneously.

Alternatively, at least one membrane matrix layer may comprise a silk fibroin membrane matrix and at least one second membrane matrix layer may comprise a biocompatible polyurethane membrane matrix. Alternatively, or in addition to, at least one third membrane matrix layer may be present comprising a membrane matrix of both silk fibroin and biocompatible polyurethane.

By preparing the membranes of the invention from silk fibroin, the inventors have developed improved membrane matrixes that can withstand strain without tearing or breaking; that are strong and resilient, compared to most other natural and synthetic silk fibroin biomaterials. The strength and resilience of a material can be defined as, the ability of a material to elongate without breaking or shattering.

The resilience of the membrane matrix to withstand strain without tearing or breaking can be varied by altering the content of the biocompatible polyurethane. Ideally the membrane can remain elastic when extended by up to 300%. That is it can deform up to 300% and still return to its original length. Silk on its own is brittle when dry but even when wet, it often deforms plastically at higher % elongation. In a particular form of the invention, the membrane will have a percentage of elongation between 5 and 300%. Low elongation is associated with a brittle material. Brittle materials often have higher tensile strength and high modulus but low elongation.

Where the membranes are formed as a bioscaffold for tissue engineering, the percentage of elongation can be as low as 5% MPa, if required and as high as 300% or greater depending on the use to which the membrane will be applied. Desirably, the percentage of elongation of the membrane matrix is in the range of 50 to 250 percentage with percentages of elongation of 5, 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300% or any value in between these numbers, being acceptable.

Where the membrane matrix is used as a scaffold for repair of, for example, bone or in wound repair the percentage of elongation of the membrane can be between 5 to 200%. Alternatively, where the membrane matrix is used as a device for repair of tympanic membranes the percentage of elongation of the material will be in the range of 80 to 170%.

The use of biocompatible polyurethane in combination with silk fibroin in materials processing also expands the functional features attainable with silk fibroin, and the formation of more flexible membranes with potential utility in biomaterial and device applications.

A membrane of the device of the invention may possess a Young's modulus in the order of 5 to 2000 MPa. For example, the Young's modulus can be 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1011, 1012, 1013, 1014, 1015, 1016, 1017, 1018, 1019, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990 or any value in between. Ideally the Young's modulus will be matched to the use to which the membrane is to be used. For example, where the membrane matrix is used as a scaffold repair of bone or in wound repair the Young's modulus may be between 400 MPa and 2000 MPa. Alternatively, where the membrane matrix is used as a device for repair of tympanic membranes the Young's modulus of the material will be in the range of 100 to 500 MPa. For example, such a membrane matrix can have a Young's modulus of 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 MPa or any value in between these numbers.

This Young's modulus value is selected to substantially match size of perforation and acoustic properties. A Young's Modulus of approximately 200, 210, 220, 230, 240, 250, 260, 270, 280, 290 or 300 MPa is preferred. In this respect sound transmission to the middle ear ossicles is dependent on the "stiffness" of a graft comprising the device and is an important issue in large perforations for an instant improvement in hearing outcomes.

When the membranes of the invention are used in a biological setting such as bio-scaffolds or in the repair of damaged tissue including, without limitation, in wound repair, as a substitute for bone or in the repair of tympanic membranes, the membrane is adapted to facilitate cellular adhesion for efficient growth and proliferation of cells across the membrane. The silk fibroin membrane matrixes of the invention therefore provide a construct for tissue engineering. They provide a matrix upon which keratinocytes, fibroblasts, glia, osteoblasts, osteoclasts, epithelium, endothelial cells, chondrocytes etc. may grow. The membrane matrix may also be used in cell therapies using induced pluripotent stem cells, adult stem cells and embryonic stem cells, and combinations thereof to provide a scaffold upon which these cells can grow in a patient.

Preferably, any cell type can be added to the membranes for culturing and possible implantation, including keratinocytes, cells of the muscular and skeletal systems, such as chondrocytes, fibroblasts, muscle cells and osteocytes, and stem cells (including, e.g., embryonic stems, adult stem cells, and induced pluripotent stem cells), and combination thereof, either as obtained from donors, from established cell culture lines, or even before or after cell modification by molecular or genetic means. Pieces of tissue can also be used to engraft the construct with different cell types.

Membranes of the invention do not need to be smooth, they can possess pores or surface deformations on their surface that range between approximately 0.001 microns and approximately 200 microns in size. Where the membranes include pores, the pores may traverse the membrane or they may be closed at one end. Where the pores traverse the membrane, they may or may not support cellular growth through the membrane. Where the membranes find use as tympanic membranes they do not support transverse growth of cells through the membrane. However, where these membranes are used as bioscaffolds they can support transverse growth of cells through the membrane.

In an embodiment, the membranes include one or more pores or surface deformations on their surface having a diameter of between approximately 0.001 microns to approximately 200 microns, which facilitate cell infiltration and tissue formation. In a preferred form the pores or surface deformations have a diameter of 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 110, 120, 130, 140, 150, 160, 170, 180, 190, 200 microns or any value in between these numbers When pores are present in the membrane they will provide void volume for new tissue formation and remodelling to facilitate host tissue integration upon implantation into a subject in need of such treatment. In this respect, the device provides a structure that allows for efficient nutrient and metabolite transport whilst also maintaining mechanical stability.

The thickness of the membrane matrix will vary between approximately 1 microns and approximately 2 mm. For example, the membrane can have a thickness of 1, 2, 3, 4, 5, 6, 7, 8, 9, 10, 15, 20, 25, 30, 35, 40, 45, 50, 55, 60, 65, 70, 75, 80, 85, 90, 95, 100, 210, 215, 220, 225, 230, 235, 240, 245, 250, 255, 260, 265, 270, 275, 280, 285, 290, 295, 300, 310, 315, 320, 325, 330, 335, 340, 345, 350, 355, 360, 365, 370, 375, 380, 385, 390, 395, 400, 410, 415, 420, 425, 430, 435, 440, 445, 450, 455, 460, 465, 470, 475, 480, 485, 490, 495, 500, 510, 515, 520, 525, 530, 535, 540, 545, 550, 555, 560, 565, 570, 575, 580, 585, 590, 595, 600, 650, 700, 750, 800, 850, 900, 1000, 1050, 1100, 1150, 1200, 1250, 1300, 1350, 1400, 1450, 1500, 1600, 1650, 1700, 1750, 1800, 1850, 1900, 2000 microns.

Where the membranes are used as a replacement tympanic membrane, they will have a thickness of between approximately 10 and approximately 600 microns. Most preferably, the membrane has a thickness of between approximately 30 and approximately 100 microns. For example the membrane is in the range of 30 to 50 microns, 50 to 65 microns, 65 to 80 microns or 80 to 100 microns.

Where the membrane is being used as a scaffold, the membrane may be much thicker such as up to 2 mm. In this respect, the relative thickness of the membrane in such uses will be determined based on the speed of biodegradability and the degree of tensile strength, toughness and elasticity that the membrane must deliver for the intended use.

The membrane matrix of the invention may be biodegradable or more preferably non-biodegradable. In this respect, where the membrane is biodegradable the membranes can have a biodegradability that takes up to 2 or more years for complete dissolution. Preferably the membranes are biodegradable over 18, 19, 20, 21, 22, 23, 24 months. When used as a bioscaffold that is to be degraded when used in a subject the membranes may have a biological life of between 1 and 12 years, ideally 1, 2, 3, 4, 5, 6, 7, 8, 9, 10, 11 years. Preferably the membrane is not biodegradable or at least where the silk may biodegrade the polyurethane will not biodegrade.

Silk fibroin membrane matrices of the invention have distinct properties compared with silk fibroin films lacking polyurethane. For example, flexibility is enhanced with the use or inclusion and use of polyurethane.

The membrane matrix of the invention can also include one or more additional materials or layer thereon that are non-autologous to the subject in need of such treatment. For example, the silk membrane can include at least one additive or layer including an additive selected from an additional plasticizer, gelatin, collagen, chitosan, alginic acid, hyaluronic acid, pluronic 127, poly(ethylene glycol) (PEG), and 1,2,6-hexanetrioland and 1,3-propanediol. Further examples of additives are illustrated in Jose, R. R. et al., 2015. Polyol-Silk Bioink Formulations as Two-Part Room-Temperature Curable Materials for 3D Printing. *ACS Biomaterials Science & Engineering*, 1, pp. 780-788, which is incorporated herein by cross reference.

Materials that can be used in the membranes include any of the materials selected from the group comprising: hyaluronic acid based hydrogels (Carbylan) and films (Seprafilm); calcium alginate; poly(glycerol sebacate); water soluble and insoluble chitosan; and collagen.

The membrane matrix can also include an additional plasticizer. For example, the membrane matrix can further comprise one or more additives selected from the group comprising, amongst others, gelatin, chitosan, alginic acid, hyaluronic acid, pluronic 127, aliphatic polyester, a poly (alkylene) oxide, poly(L-lactic acid), 70/30 L-lactide/e-caprolactone co-polymer, poly(caprolactone), poly(DL-lactide-co-caprolactone), poly(D-lactide-co-caprolactone), poly(L-lactide-co-caprolactone), poly(lactide-co-glycolic acid), poly(vinylpyrrolidine), poly(dimethylsiloxane), poly (lysine), laminin, fibronectin, elastin, proteoglycans, polypeptides, poly(ethylene-co-vinyl) alcohol,1,2,6-hexanediol, 1,3-propanediol, poly(vinyl) alcohol, poly(ethylene)glycol, poly(propylene)glycol, poly-L-lactide-co-glycolide-co-ε-caprolactone, poly(tetrafluoroethylene), poly(dioxanone), polyglactin 910, or combinations thereof in order that the device is manageable in a dry state prior to use.

The silk fibroin membrane matrix produced according to the invention can also include at least one active agent either impregnated into the membrane or in the pores thereon (when present) that assist or promote the growth of cells. The active agent is preferably selected from the group consisting of vitamins, minerals, proteins (such cytokines, enzymes and cell growth modifiers including growth factors or recombinant growth factors and fragments and variants thereof), protein inhibitors, peptides, nucleic acid analogues, nucleotides or oligonucleotides, peptide nucleic acids, aptamers, antibodies or fragments or portions thereof, hormones, hormone antagonists, carbohydrates, co-factors, antibiotics or antimicrobial compounds, anti-inflammatory agents, antiproliferative agents, antihistamines, viruses, antivirals, toxins, prodrugs, chemotherapeutic agents, drugs, and combinations thereof.

Preferably, the bioactive molecules comprise any one or more bioactive molecules selected from the group comprising: epidermal growth factors including Epidermal Growth Factor (EGF), transforming growth factor-alpha (TGF-α), transforming growth factor-beta (TGF-ß), Heparin Binding Epidermal Growth Factor (HB-EGF), amphiregulin, epigen, epiregulin, betacellulin; fibroblast growth factors including acidic fibroblast growth factor (FGF-1/aFGF), basic fibroblast growth factor (FGF-2/bFGF); keratinocyte growth factors including Keratinocyte Growth Factor 1 (KGF-1/FGF-7), Keratinocyte Growth Factor 2 (KGF-2/FGF-10); insulin-like growth factors including Insulin-like Growth Factor 1 (IGF-1), Insulin-like Growth Factor 2 (IGF-2); platelet derived growth factors including Vascular Endothelial Growth Factor (VEGF), Platelet Derived Growth Factor-BB (PDGF-BB), Hepatocyte Growth Factor (HGF), cytokines including IL-6, IL-19, IL-24; extracellular matrix proteins including hyaluronic acid, fibronectin, vitronectin, laminin; and vitamins including trans-retinoic acid (vitamin A), L-ascorbic acid (vitamin C), (+)-α-tocopherol (vitamin E). More preferably, the bioactive molecules comprise any one or more bioactive molecules selected from the group comprising: hyaluronic acid; vitronectin; amphiregulin; interleukin 19 (IL-19); interleukin 24 (IL-24); transforming growth factor-alpha (TGF-α); VEGF; and fibronectin.

The membrane matrixes of the invention can be prepared as a composite of multiple membranes, in the form of a device. In such circumstances, the device can have two or more membrane layers. Each layer may be prepared with the same or different characteristics. In an alternate form of the invention a composite device can be prepared where one or more membranes are layered over another surface. That surface can be prepared of any material suitable for use in the way the device is to be utilised. Where the membrane is being used for tissue engineering the surface onto which the membrane is layered is preferably of a type that is biocompatible. The surface may be prepared from another material that is more rigid or has a greater tensile strength than the membrane.

Where the membrane is prepared as a device, there may be one or more membrane layers in the device. The thickness of each layer in the device will vary between approximately 10 microns and approximately 2 mm. Preferably, where the membranes are used as a replacement tympanic membrane will have a thickness of between approximately 5 and approximately 100 μm. Most preferably, the one or more membrane layers have a combined thickness of between approximately 10 and approximately 80 μm.

Where the device of the invention includes layers that are prepared from materials that are different from that produced by the method of the invention those materials can be of any source, such as a source non-autologous to the subject treated. Such materials can be of a non-mammalian source. Alternatively, they can be selected from the group comprising, amongst others, decellularised tissue from non-autologous mammalian membranes, including tympanic membrane, pericardium, periosteum, dermis, muscle fascia. Such additional materials may be appropriate particularly where the device is deployed in reconstructive surgery.

Fabrication of a Silk Fibroin Membrane Matrix

In a third aspect, the invention provides a method of fabricating a silk fibroin biocompatible polyurethane membrane matrix comprising the steps of:
 a. preparing silk protein or a silk protein complex solution after removal of sericin from a cocoon or fibre;
 b. dissolving biocompatible polyurethane and silk fibroin using a solvent; and
 c. drying the prepared solution to fabricate a silk fibroin biocompatible polyurethane complex.

The resultant product is then cast into membrane mound to form films, or membranes. These films when assessed for mechanical properties and structural features displayed enhanced properties, perhaps enacted by affecting silk fibroin crystallization behaviour in the formation of the β-sheets as the stabilizing hydrogen bonded cross-links in the films.

According to step (b) of this method of fabrication the biocompatible polyurethane and silk fibroin are dissolved using a solvent such as hexafluoroisopropanol, N,N-Dimethylacetamide (DMAc) or dimethylformamide (DMF). Preferably, the biocompatible polyurethane and silk fibroin are dissolved using a salt such as LiBr that is dissolved in a solvent such as hexafluoroisopropanol, N,N-Dimethylacetamide (DMAc) or dimethylformamide (DMF).

Alternatively, the Fibroin can be dissolved in concentrated aqueous solutions of acids such as phosphoric, formic, sulfuric, hydrochloric or in concentrated aqueous, organic and aqueous-organic solutions of salts. Silk is also soluble in lithium halides in organic solvents (dimethylacetamide (DMAc) and dimethylformamide (DMF)). For example, a 10.0% solution of fibroin can be obtained at 50 C in a 2-3 M solution of LiBr in DMAA or DMF and in 9.5-10 M solution of LiBr in water. Fibroin also dissolves in concentrated aqueous solutions of acids (phosphoric, formic, sulfuric, hydrochloric) and in concentrated aqueous, organic, and aqueous organic solutions of salts such as LiCNS, LiBr, $CaCl_2$, $Ca(CNS)_2$, $ZnCl_2$, $NH_4CNS$, $CuSO_4+NH_4OH$, $Ca(NO_3)_2$. Further aqueous solutions of $ZnCl_2$ are the most effective solvents, whereas in solutions of $ZnCl_2$ in DMAA, DMF, and N-methyl-2-pyrrolidone, fibroin dissolves only at 155 C to form relatively dilute solutions (1.0 2.0 wt %). Aqueous and aqueous-organic solutions of LiCl, LiBr, NaSCN, and KSCN also dissolve up to 20 wt % fibroin; the solvency of mixtures increases with a decrease in the relative content of water in the solvent: see Sashina et al., 2006 RUSSIAN JOURNAL OF APPLIED CHEMISTRY Vol. 79 No. 6 869 to 876 the full text of which is incorporated herein by reference.

The process of removing sericin from a cocoon or raw silk refers to degumming. Such degumming processes are well known to those skilled in the art. For example, examples of the degumming processes include (1) a method of boiling soap, sodium carbonate and the like in an alkali aqueous solution, (2) a degumming method using a protease extracted from *Aspergillus* sp. and the like, and (3) a high temperature high pressure method using a high temperature and high pressure pot.

In one illustrative form of the second aspect of the invention, the method of fabrication includes the steps of:
 a) degumming silk fibres;
 b) drying the degummed fibres of step (a) and dissolving the product in a chaotropic salt.

c) dialyzing the silk solution of step (b) against dH$_2$O to obtain a silk solution;
d) Freeze-drying the silk solution of step (c)
e) Adding the polyurethane and dissolving the composition of step (d) in a solvent such as hexafluoroisopropanol, N,N-Dimethylacetamide or dimethylformamide; and
f) fabricating the solution of step (e) into a membrane matrix.

The silk protein or silk protein complex solution may be dissolved using a chaotropic salt composed of at least one compound or an ethanol aqueous solution including the same selected from lithium bromide (LiBr), lithium chloride (LiCl$_2$), zinc chloride (ZnCl$_2$) and calcium chloride (CaCl$_2$), lithium thiocyanide (LiSCN). Preferably lithium bromide is used.

In another illustrative form of the invention, the method of fabrication includes the steps of:
a) degumming silk fibres;
b) drying the degummed fibres of step (a) and dissolving the product in a chaotropic salt solution.
c) dialyzing the silk solution of step (b) against dH$_2$O to obtain a silk solution;
d) Freeze-drying the silk solution of step (c) to form a silk foam; and
e) dissolving a biocompatible polyurethane in a solvent such as hexafluoroisopropanol (HFIP), N,N-Dimethylacetamide (DMAc) or dimethylformamide (DMF), then casting it into a membrane mould to evaporate; or
f) melting a biocompatible polyurethane by heating and (f1) casting it into a membrane mould to cool, or (f2) injection moulding into a membrane mould and allowing the membrane to cool; and
g) optionally treating the surface of the membrane of step (e) or (f) by at least one of: application of plasma, adsorption of biomolecules or surfactants, covalent grafting of hydrophilic compounds, polymerisation, uv treatment, chemical etching, ozone treatment, layer by layer adsorption, electrodeposition or electrochemical etching;
h) using the aqueous silk product of step (c) to coat the membrane of step (e) or (f); or
i) dissolving the silk foam of step (d) in a suitable solvent such as HFIP or Formic acid and coating the membrane of step (e) or (f).

Device for the Otological Repair

In a fourth aspect, the invention provides a device for the repair of an otological condition such as a perforation, and particularly a chronic perforation comprising a membrane matrix as described herein.

Preferably the silk fibroin membranes described herein are fabricated for repair of tympanic membrane perforations. A membrane matrix suitable for such repair preferably will have a tensile strength between 5 MPa to 100 MPa, more preferably approximately 10 MPa to 95 MPa, and desirably a tensile strength between approximately 10 and approximately 50 MPa.

When such a membrane is used for repair of perforations of a tympanic membrane the membrane must conduct sound waves. In this respect the membrane of the invention should possess vibroacoustic characteristics substantially consistent with or greater than that of native tympanic membranes or of cartilage used for tympanic membrane reconstruction. Vibroacoustic characteristics are related to the tensile strength, elasticity and the thickness of the device as discussed above. Further, sound transmission to the middle ear ossicles is also dependent on the "stiffness" of the device. Stiffness is an important issue in large perforations for an instant improvement in hearing outcomes. The specific tensile strength of the one or more membranes facilitates optimal acoustic transmission resulting in improved hearing outcomes for a subject treated with the membrane immediately following placement.

Preferably the membrane described herein will have a strength, elasticity, thickness and "stiffness" to conduct sound waves between 20 Hz and 20 KHz to the middle ear in vivo.

Any engineered membrane construct of the invention described herein may possess a peripheral skirt around the membrane that is adapted for reconstructive surgery. This may be in addition to or as part of the tympanic annulus. In this respect the device may be substantially thickened at its periphery allowing the membrane to be used in mastoidectomy surgery (including Radical Mastoidectomy, Canal Wall Down Mastoidectomy, Canal Wall Up Mastoidectomy, Cortical Mastoidectomy, Modified Radical Mastoidectomy) done as part of treatment for mastoiditis, chronic suppurative otitis media or cholesteatoma.

The term "periphery," as used herein in the context of silk membranes, refers to the boundary line encompassing the plane of the membrane. The periphery of a membrane is not necessarily circular and need not be of the same thickness of the membrane. For example, the periphery of the membrane may be up to 5 mm thick down to 10 microns and will include any thickness in between.

While the membrane described herein may incorporate a peripheral skirt the membrane will transmit sound waves between 20 Hz and 20 KHz to the middle ear in vivo.

In a preferred embodiment, the membrane has a tensile strength of between 5 MPa to 100 MPa.

The membrane of the invention possesses vibroacoustic characteristics substantially consistent with or greater than that of native tympanic membranes or of cartilage used for tympanic membrane reconstruction.

When used in repair of a tympanic membrane of a subject in need of such treatment, the membrane can transmit sound waves between 20 Hz and 20 KHz to the middle ear ossicles.

Vibroacoustic characteristics are related to the tensile strength, elasticity and the thickness of the device. They are preferably optimized for the conduction of sound.

Sound transmission to the middle ear ossicles is dependent on the "stiffness" of the device. Stiffness is also an important issue in large perforations for an instant improvement in hearing outcomes. The specific stiffness of the one or more membranes provides resistance to rupture and facilitates optimal acoustic transmission resulting in improved hearing outcomes for a subject treated with the device immediately following placement.

A membrane of the device of the invention also possesses a tensile strength between 5 MPa to 100 MPa. This value is selected from within the range so as to substantially match size of perforation and acoustic properties.

In a preferred embodiment, the device has a tensile strength of 10 MPa to 50 MPa. More preferably, the device of the invention has a tensile strength of 30 MPa to 50 MPa. Such tensile strength is particularly useful for treating perforations in the pars tensa which is the most common area for a perforation.

Where the invention provides the membrane for repair of tympanic membrane perforations, and particularly a chronic perforation the membrane matrix layer is substantially disc-like shaped having two ovoid or substantially circular faces on opposing sides of the membrane. Preferably, one or both faces have a diameter of between approximately 3 mm and approximately 25 mm, and more preferably between approximately 10 mm and approximately 20 mm. Preferably, one or both ovoid faces of the device have diameters of approximately 9 mm and approximately 8 mm. Even more preferably, one or both ovoid faces of the device have diameters of approximately 6 mm and approximately 5 mm. Most preferably, one or both faces of the device are substantially circular and have an optimal diameter of approximately 9.5-10 mm and a range 5-15 mm.

The membrane matrix of the invention can be trimmed post-production to match the size and shape of a region to be repaired. This trimming can be carried out using an appropriate cutting device such as surgical scissors. The device can also be manipulated post production by scoring or cutting grooves in one or more surfaces of the device to improve the flexibility or bendability of the device, or to allow it to fold and substantially maintain its folded conformation.

In addition, the membrane may present other properties. The invention will now be described in relation to those preferred properties.

A. Transparency

The device of the invention is at least partially translucent. Preferably 10, 15, 20, 25, 30, 35, 40, 45, 50, 55, 60, 65, 70, 75, 80, 85, 9091, 92, 93, 94, 95, 96, 97, 98 99 and 100% transparent, which can assist in post treatment examination of the ear drum and middle ear of a subject treated with the device.

The device of the invention may be transparent or translucent, similarly, to an undamaged tympanic membrane. This also enables examination of the middle ear of a subject for infection or defects during follow up after repair of the tympanic membrane using the device.

B. Biodegradability

In a preferred form, the device is biodegradable having a biological life of at least 12 months. Preferably the device will have a life expectancy of at least 36 months.

An in vivo biological life of between 12 and 36 months is preferred because the device must remain in place until such a time that complete or substantially complete wound closure has occurred. Typically, in tissue engineering it is advantageous to have the device in vivo for a minimal amount of time to prevent possible long term complication such as cyst formation. For example, small perforations may heal in a relatively short period of time (approximately 2 weeks for closure, plus 4-6 weeks for complete remodelling), while larger perforation may take significantly longer requiring up to 12 months for complete cellular remodelling of the neo-tympanum. The biomechanical properties of the device have been selected to substantially prevent later complications such as atrophy and retraction including cholesteatoma in a subject treated using the device.

C. Cellular Adhesion

In an embodiment of the invention the membrane is adapted to facilitate cellular adhesion for efficient growth and proliferation of cells across the membrane.

Any type of cell can be added to the tissue-engineered construct for culturing and possible implantation, including keratinocytes, cells of the muscular and skeletal systems, such as chondrocytes, fibroblasts, muscle cells and osteocytes, and stem cells (including, e.g., embryonic stems, adult stem cells, and induced pluripotent stem cells), and combination thereof, either as obtained from donors, from established cell culture lines, or even before or after cell modification by molecular or genetic means. Pieces of tissue can also be used to engraft the construct with different cell types. Preferably the membrane structure controls or prevents infiltration of cells through it into the middle ear when in use, such as to prevent the movement of keratinocytes to the middle ear in cholesteatoma.

In one form of this embodiment the membrane will possess pores or surface deformations that range between approximately 0.001 μm and approximately 5 □m. In another form of this embodiment, the pores within the body of the membrane have a diameter of between approximately 5 □m and approximately 200 □m to facilitate cell infiltration and tissue formation of the middle layer.

When pores are present in the membrane they will provide void volume for new tissue formation and remodeling so as to facilitate host tissue integration upon implantation into a subject in need of such treatment. In this respect, the device provides a structure that allows for efficient nutrient and metabolite transport whilst also maintaining mechanical stability.

Surface pores or deformations when present will support proliferation, migration and/or adhesion of at least keratinocytes when grafted to the perforated tympanic membrane or ear canal of a subject in need of such treatment. This is in order to facilitate the repair and regeneration of the tympanic membrane from damage such as from a chronic perforation. Thus, the device of the invention provides a scaffold to enable the accelerated closure of a chronic tympanic membrane perforation or a defective portion of ear canal soft tissue and bone via natural wound healing processes.

D. Thickness

The thickness of a device of the invention will vary depending on factors such as the vibroacoustic properties and mechanical properties required from the membrane, the number of membrane layers or the size of the tympanic membrane perforation or defective portion of ear canal in a subject treated using the device. According to the invention the membrane must transmit sound waves between 20 Hz and 20 KHz to middle ear ossicles. Within the confines of this parameter the membrane can be prepared as a single layer prepared according to the method of the invention. Alternatively, the device can have a plurality of layers formed by the product of the method of the invention together with other layers produced from a range of different materials. Where there is a plurality of layers, the membrane portion of the device must transmit sound waves between 20 Hz and 20 KHz to the middle ear ossicles.

Provided the membrane portion of the device transmits sound waves between 20 Hz and 20 kHz to the middle ear ossicles, the skirt of the membrane may be of greater thickness. This is desirable where reconstructive surgery is appropriate. In this respect the device may be substantially thickened at its periphery to accommodate surgical requirements during mastoidectomy (including Radical Mastoidectomy, Canal Wall Down Mastoidectomy, Canal Wall Up Mastoidectomy, Cortical Mastoidectomy, Modified Radical Mastoidectomy) done as part of treatment for mastoiditis, chronic suppurative otitis media or cholesteatoma.

The term "periphery," as used herein in the context of silk membranes, refers to the boundary line encompassing the plane of the membrane. The periphery of a membrane is not necessarily circular and need not be of the same thickness of the membrane. For example, the periphery of the membrane may be up to 5 mm thick down to 10 microns and will include any thickness in between.

For the purposes of describing the invention, the terms "membrane", "membrane matrix", "membrane layer", "membrane matrix layer", "fibrous membrane" and "film" may be used interchangeably.

In a preferred form, the device has between one and three membranes layered adjacent to each other. Thus, the device can consist of a single membrane, two membranes or three membranes.

The membrane layers of the device have a thickness which is measured as the distance between the exposed faces of the one or more membranes on the exterior of the device.

Membrane layers will have a combined thickness of between approximately 1 and approximately 600 microns. Said thickness though must be selected to transmit sound waves between 20 Hz and 20 KHz to middle ear ossicles. Variability in the construct of the membrane within the scope of this parameter is to be recognized. Preferably, the membrane layers which meet this parameter have a combined thickness of approximately 10 and approximately 300 microns. Most preferably, the membrane layers have a combined thickness of between approximately 30 and approximately 150 microns. By way of illustration the membrane layers have a combined thickness of approximately 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590 and approximately 600 microns.

Where the membrane includes more than one layer, at least one of the layers can include fibrous material.

In various aspects, fibrous membranes are disclosed comprising at least a first layer comprising a silk fibroin biocompatible polyurethane membrane matrix prepared according to the method of the invention and a second layer having a composition of materials that may be the same or different to the first layer. Where there are multiple layers, the layers will preferably be arranged such that any fibers in each layer are aligned.

The silk membrane can include at least one additive selected from an additional plasticizer, gelatin, collagen, chitosan, alginic acid, hyaluronic acid, pluronic 127 and poly(ethylene glycol) (PEG).

E. Layer Composition

In one embodiment of the invention, the device may comprise multiple layers, wherein at least one layer is comprised of silk fibroin, and at least one layer is comprised of biocompatible polymer.

In another embodiment, the device may comprise multiple layers wherein at least one layer is comprised of a silk fibroin membrane matrix and/or at least one layer is comprised of biocompatible polyurethane membrane matrix and/or at least one layer is a combined silk fibroin/biocompatible polyurethane membrane matrix.

In another embodiment of the invention, multiple layers may be present, wherein at least one layer is a membrane matrix in accordance with the present invention and at least one layer is comprised of a material which is different from that of the present invention.

In this embodiment, materials that may be used in a layer of the membranes that are employed to produce a device include any of the materials selected from the group comprising: hyaluronic acid based hydrogels (Carbylan) and films (Seprafilm); calcium alginate; poly(glycerol sebacate); water soluble and insoluble chitosan; and collagen.

Collagen is a major extracellular matrix component, has physical characteristics including high tensile strength, flexibility, non-reactivity, non-toxicity and non-carcinogenicity. As the main constituent of the lamina propria of the tympanic membrane, collagen helps to maintain the resilience and integrity of tympanic membrane and hence plays a key role in hearing.

One or more layers employed in the device may include a plasticizer.

For example, the device of the invention may further comprise one or more additive selected from the group comprising, amongst others, glycerol, gelatin, chitosan, alginic acid, hyaluronic acid, pluronic 127, aliphatic polyester, a poly(alkylene) oxide, poly(L-lactic acid), 70/30 L-lactide/ε-caprolactone co-polymer, poly(caprolactone), poly(DL-lactide-co-caprolactone), poly(D-lactide-co-caprolactone), poly(L-lactide-co-caprolactone), poly(lactide-co-glycolic acid), poly(vinylpyrrolidine), poly(dimethylsiloxane), poly(lysine), collagen, laminin, fibronectin, elastin, alginate, fibrin, hyaluronic acid, proteoglycans, polypeptides, poly(ethylene-co-vinyl) alcohol, poly(vinyl) alcohol, poly(ethylene)glycol, poly(propylene)glycol, poly-L-lactide-co-glycolide-co-ε-caprolactone, poly(tetrafluoroethylene), poly(dioxanone), polyglactin 910 and combinations thereof in order that the device is manageable in a dry state prior to use. Also, one or more cross-linkers may also be used to covalently bond the silk and polyurethane. Examples (used with silk) include: Glutaraldehyde, Genipin, Horseradish peroxidase (HRP) with hydrogen peroxide ($H_2O_2$), Tyrosinase (eg Mushroom tyrosinase) or transglutamase (eg microbial transglutamase)-enzymatic cross-linking, Ethylene glycol based systems: eg. polyethylene diglycidyl ether (PEGDE), ethylene glycol, diglycidyl ether (EGDE), Tris(2,2'-bipyridyl)dichlororuthenium(II) hexahydrate with sodium persulfate (SPS) or ammonium persulfate (APS) and, 1-ethyl-3,3-dimethylaminopropyl-carbodiimide (EDC)-N-hydroxysuccinimide The aliphatic polyester can be selected from D-lactide, L-lactide, poly(lactic acid), poly(lactide)glycolic acid, poly(glycolic acid), poly(glycolide), glycolide, poly(lactide-co-glycolide), poly(lactic acid-co-glycolic acid), epsilon-caprolactone, poly(epsilon-caprolactone) and a combination thereof. The poly(alkylene) oxide can be selected from poly(ethylene) oxide and poly(propylene) oxide.

Where the device of the invention includes layers that are prepared from materials that are different from that produced by the method of the invention those materials can be of any source, such as a source non-autologous to the subject treated. Such materials can be of a non-mammalian source. Alternatively, they can be selected from the group comprising, amongst others, decellularised tissue from non-autologous mammalian membranes, including tympanic membrane, pericardium, periosteum, dermis, muscle fascia. Such additional materials may be appropriate particularly where the device is deployed in reconstructive surgery.

F. Active Agent in a Membrane Matrix

In an embodiment the membrane matrix includes at least one active agent. The active agent can be cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antibacterial agent/antimicrobial compounds, viruses, antivirals, toxins, prodrugs, chemotherapeutic agents, small molecules, drugs, or combinations thereof.

For example, membranes of the invention can include a range of biocompatible active agents that support proliferation, migration and/or adhesion of tympanic membrane keratinocytes following in vivo implantation as well as in vitro culture. Preferably, biomaterials are selected that provide that the device is relatively soft.

According to this embodiment there is provided a method of embedding at least one active agent in a silk fibroin biocompatible polyurethane membrane matrix, comprising blending a silk fibroin and/or biocompatible polyurethane solution with at least one active agent, wherein the active agent is not deactivated by a solvent such as hexafluoroisopropanol or dimethylformamide treatment; casting the solution onto a film-supporting surface; and drying the film.

In an alternate embodiment there is provided a method of impregnating at least one active agent into the membrane matrix, comprising casting the silk fibroin and/or biocompatible polyurethane solution produced according to the invention onto a film-supporting surface; and drying the film in the presence of the active agent.

Bioactive molecules incorporated or soaked into the membrane of the invention include agents that assist or promote growth of cells of the ear drum. Bioactive molecules can be bound to the surface of the device or located in pores of the device.

Bioactive molecules include molecules selected from the group: vitamins, proteins, peptides, enzymes, carbohydrates, co-factors, nucleotides (DNA or RNA or derivatives thereof), small organic molecules (for example, drugs), antibiotics, antiviral agents, antimicrobial agents, anti-inflammatory agents, antiproliferative agents, cytokines, protein inhibitors, antihistamines. Preferably the bioactive molecules comprise any one or more bioactive molecules selected from the group comprising: epidermal growth factors including Epidermal Growth Factor (EGF), Transforming Growth Factor-alpha (TGF-α), Transforming Growth Factor-beta (TGF-ß) Heparin Binding Epidermal Growth Factor (HB-EGF), amphiregulin, epigen, epiregulin, betacellulin; fibroblast growth factors including acidic Fibroblast Growth Factor (FGF-1/aFGF), basic Fibroblast Growth Factor (FGF-2/bFGF); keratinocyte growth factors including Keratinocyte Growth Factor 1 (KGF-1/FGF-7), Keratinocyte Growth Factor 2 (KGF-2/FGF-10); insulin-like growth factors including Insulin-like Growth Factor 1 (IGF-1), Insulin-like Growth Factor 2 (IGF-2); platelet derived growth factors including Vascular Endothelial Growth Factor 165 ($VEGF_{165}$), Platelet Derived Growth Factor (PDGF), cytokines including IL-6, IL-19, IL-24; extracellular matrix proteins including hyaluronic acid, fibronectin, vitronectin, laminin; and vitamins including trans-retinoic acid (vitamin A), L-ascorbic acid (vitamin C), (+)-α-tocopherol (vitamin E). More preferably, the bioactive molecules comprise any one or more bioactive molecules selected from the group comprising: hyaluronic acid; vitronectin; amphiregulin; interleukin 19 (IL-19); interleukin 24 (IL-24); transforming growth factor-alpha (TGF-α); VEGF; and fibronectin.

The concentration of bioactive molecules is preferably between 5 ng/ml and 150 μg/ml.

When hyaluronic acid is present in the silk membrane it will be at a concentration preferably between approximately 1 μg/ml and approximately 10 μg/ml, and more preferably at approximately 5 μg/ml.

When vitronectin is present in the silk membrane it will be at a concentration preferably between approximately 0.1 μg/ml and approximately 1.0 μg/ml, and more preferably at approximately 0.5 μg/ml.

When amphiregulin is present in the silk membrane it will be at a concentration preferably between approximately 20 ng/ml and approximately 100 ng/ml, and more preferably at approximately 60 ng/ml.

When IL-19 or IL-24 is present in the silk membrane it will be at a concentration preferably between approximately 20 ng/ml and approximately 100 ng/ml, and more preferably at approximately 60 ng/ml.

When TGF-α is present in the silk membrane it will be at a concentration preferably between approximately 20 ng/ml and approximately 140 ng/ml, and more preferably at approximately 80 ng/ml.

When VEGF is present in the silk membrane it will be at a concentration preferably between approximately 60 ng/ml and approximately 200 ng/ml, and more preferably at approximately 100 ng/ml.

The silk fibroin biocompatible polyurethane membranes of the invention may be used in the formation of a medical device. The bioactive molecules can be added during formation of the device and/or can be added separately to the device after the device is formed and/or during implantation or grafting of the device.

The device can comprise any of the compounds listed herein, without limitation, individually or in any combination. Any of the bioactive molecules listed herein may be formulated by known methods for immediate release or extended release. Additionally, the device can comprise two or more bioactive molecules in different manners, for example, amongst others, the device may be impregnated with one biologically active compound and coated with another. In another embodiment, the device comprises one bioactive molecule formulated for extended release, and a second biologically active compound formulated for immediate release.

Wound healing including the repair of tympanic membranes requires sufficient nutrition. Wound healing nutrients include a source of zinc, iron, vitamin C, arginine, and other bioactive molecules. Therefore, the device can be impregnated or coated with a physiologically-available form of one or more of these nutrients required for wound healing. It is preferred that these nutrients are formulated for extended release.

In a preferred embodiment, proteins, polypeptides or peptides (including antibiotics) that are utilised as immunomodulatory agents are preferably derived from the same species as the subject in need of repair to the tympanic membrane or defective portions of the ear canal. For example, where the subject is a human, the proteins, polypeptides or peptides that are used as immunomodulatory agents are preferably human or humanised to reduce the likelihood of an immune response to the proteins, polypeptides or peptides.

Bioactive molecules are considered to enhance the growth, migration and/or proliferation of cells including tympanic membrane keratinocytes and mucosal cells, over, or into, the device in vivo as it is used as a graft to facilitate closure of a perforation in a tympanic membrane or defective portions of the ear canal for a subject in need of such therapy. In addition, it is expected that these bioactive molecules would provide biological signals to allow for post healing remodelling of the wound site with the intention to restore functionality to that of a substantially premorbid state, thereby enhancing healing and hearing outcomes in the long term for said subject. The device of the invention may not include bioactive molecules; however, the closure time for repairing a tympanic membrane or an ear canal in a subject in need of such therapy may be reduced when compared to use of a device comprising bioactive molecules.

In another embodiment of the invention the silk fibroin biocompatible polyurethane membrane produced according to the method of the invention can be adapted to a variety of applications ranging from heavy-duty or high-strength reconstruction applications. For example, the peripheral skirt of the membrane can be adapted to form a reconstruction material or a tissue engineering or reconstruction scaffold. In some embodiments, the composite material can be adapted to form a surgical tool for orthopedic applications. In some embodiments, the composite material can be adapted to form a bone scaffold material. In these embodiments, the bone scaffold material can comprise an osteoconductive agent, an osteoinductive agent, an osteogenic agent, or any combination thereof.

Manufacturing

While the silk fibroin biocompatible polyurethane membrane of the invention is cast, the invention contemplates the formation of multiple layers in a membrane. To this extent, layers not formed by the method of the invention may be formed separately before being attached during production of the device. Alternatively, membrane layers may be created by folding the device.

Methods for preparing the additional layers suitable for use in developing a multilayered device include at least any one or more of: spinning including electrospinning; weaving including microweaving; or casting or dip coating.

Woven methods may include the use of a microweaving device similar to a standard textile loom albeit on a micro scale. The result is a substantially orderly woven material, Non-woven methods may include casting, amongst others. Casting involves placing a volume of solubilised fibroin solution containing fibres into a casting vessel and allowing the liquid to evaporate, leaving behind a solid cast of the fibroin protein.

Electrospinning uses an electrical charge to draw very fine (micro or nano scale) fibroin fibres from a liquid solution of the protein. It is particularly suited to the production of fibers using large and complex molecules.

Such methods for preparing the device produce pores within and on the surface of the device. Shapes and sizes of the pores will vary depending on the method used to prepare the device.

H. Size and Shape

Where the device is used in tympanic membrane repair, the device exists as a substantially disc-like shape having two ovoid or substantially circular faces on opposing sides of the device.

Such a device can be formed in any size, shape or conformation that will facilitate its use in the repair of a perforated tympanic membrane. For example, the device can be formed into a size, shape or conformation that will facilitate the occlusion of a tympanic membrane perforation, particularly in the context of a type 1 tympanoplasty or myringoplasty.

In another form, the device is formed into a shape or conformation that facilitates reconstruction of the ear canal, pars flaccida and attic region. Thus the device is adapted to conform to a defective portion of ear canal soft tissue and bone. This may include folding of the device or scoring of one or more sides of the device such that the modified conformation of the device is maintained. Thus, the size, shape and conformation of the device will be sufficient to cover or fit within the defective portion of ear canal.

Where the device is used for reconstructive surgery of the middle ear it comprises a disc like shape similar to a native tympanic membrane surrounded by a skirt formed by a plurality of layers of the membrane. The skirt provides the basis for reconstructive building of tissue removed during operations.

Accordingly, yet another aspect provided herein relates to a method of repairing or replacing a diseased or damaged bone tissue in a subject, which comprises placing at a target site of the diseased or damaged bone tissue a bone scaffold material comprising at least one layer including a silk fibroin biocompatible polyurethane membrane, or at least two layers, wherein at least one layer is a silk fibroin membrane and at least one layer is a biocompatible polyurethane membrane.

In some embodiments, the bone scaffold material can further comprise an osteoconductive agent, an osteoinductive agent, an osteogenic agent, or any combinations thereof.

In some embodiments, the bone scaffold material can further comprise a cell (e.g., a stem cell). In these embodiments, the bone scaffold material described herein can be used as a temporary, biodegradable support conduit for cell(s) to grow (e.g., native cells or exogenously-added cells) and replace with extracellular matrix, thus further improving biochemical properties over time.

The front face of a device of the invention can be of a shape other than ovoid or circular which could be selected according to the dimensions of a tympanic membrane perforation or defective portion of ear canal.

The front face of the device of the invention can comprise a variety of sizes. In a preferred form, the front face is an ovoid shape or substantially circular shape having a diameter of approximately 10 mm to 20 mm, and more preferably a diameter of approximately 15 mm. In first desired form, the front face is an ovoid shape having a diameter of approximately 9 mm by approximately 8 mm. In a second desired form, the front face is an ovoid shape of approximately 6 mm by approximately 5 mm. In a third desired form, the front face is a substantially circular shape with a diameter of approximately 3 mm.

The device may be trimmed from around the outer edge of the front face thereby customising said device for repair of a tympanic membrane perforation or defective portion of ear canal that is smaller than an available device.

The device of the invention can be trimmed post-production to match the size and shape of a region of the ear drum requiring repair. This trimming can be carried out using an appropriate cutting device such as laser cutting or with surgical scissors. The device can also be manipulated post-production by scoring or cutting grooves in one or more surfaces of the device to improve the flexibility or bendability of the device, or to allow it to fold and substantially maintain its folded conformation.

Preferably, both faces have a diameter of between approximately 3 mm and approximately 25 mm, and more preferably between approximately 10 mm and approximately 20 mm. Preferably, both ovoid faces of the device have diameters of approximately 9 mm and approximately 8 mm. Even more preferably, both ovoid faces of the device have diameters of approximately 6 mm and approximately 5 mm. Most preferably, both faces of the device are substantially circular and have a diameter of approximately 3 mm.

One or both faces of the device may be scored or grooves cut using a variety of different tools including cutting tools such as scissors or a knife or blade.

I. Kits

The invention also provides a kit for use in the repair of an ear canal, a tympanic membrane perforation, and/or the pars flaccida of a subject, said kit comprising a device as herein described. The kit may also comprise one or more solutions of any of the bioactive molecules as herein described. The one or more solutions of bioactive molecules may be for application to the device prior to implantation of the device into a subject, or for application to the device following implantation or grafting of the device to the ear drum of the subject which may occur once, or on multiple occasions thereafter.

The device of the invention may be provided in the form of a kit for the facilitation of the repair of a tympanic membrane or reconstruction of an ear canal. In this respect, the device in the kit may be provided in a wrapping or a container and in a sterile form. The kit may comprise one or more devices of the same or different sizes and any other medical device, disposable or drug that would facilitate repair of a tympanic membrane or ear canal. Preferably, a device in the kit would be provided in a sterile container or wrapping separate from the remainder of the kit contents. The kit may also comprise a support for the device of a natural or synthetic material, for example, amongst others, a plastic film or sheet. Said disposables may include one or more of bandages, sterilization means for sterilizing the tympanic membrane and the surrounding skin, gloves, sterile sheets, swabs, antibiotic cream or ointment. In one embodiment, said kit comprises at least one device and one or more bioactive molecules. The kit may also comprise bioactive molecules for applying to the device prior to implantation or grafting to the subject. The bioactive molecules may be in the form of one or more solutions. In addition or alternatively, the bioactive molecules may be applied to the ear drum of the subject being treated with the device after the device has been implanted or grafted. This may be immediately and/or in a sequence of treatments over a period of hours or days after implantation.

J. Method of Use

In a further aspect, the invention provides a method for repairing the ear drum, and more preferably a tympanic membrane perforation such as a chronic tympanic membrane perforation, and/or a defective pars flaccida and/or the scutum bone, in a subject in need of such treatment, said method comprising using the device as herein described.

The invention further provides a method for repairing a tympanic membrane perforation in a subject in need of such treatment, said method comprising using the device of the invention as described herein.

The invention provides that the use of the device to repair a tympanic membrane perforation may be the sole treatment of the tympanic membrane, or may be in addition to other therapies or treatments used simultaneously or concomitantly in the course of treating or repairing a tympanic membrane. For example, the invention provides for the repair of a tympanic membrane comprising contacting the tympanic membrane with the device, and treating the tympanic membrane using an additional therapy not comprising contacting the tympanic membrane with the device, wherein the contacting and the additional therapy individually or together cause a measurable improvement in, maintenance of, or lessening of the worsening of, at least one aspect of tympanic membrane damage.

In another aspect, the invention provides for the use of a device as herein described for supporting proliferation, migration and/or adhesion of at least the cells of an ear drum when grafted or applied to the ear drum of a subject, or more preferably, the tympanic membrane such as a perforated pars tensa of tympanic membrane of a subject, and/or the pars flaccida and/or the scutum bone of a subject. The invention also provides for the use of a device as herein described in mastoid obliteration techniques for reconstruction of an ear canal of a subject after tympanomastoidectomy, including to cover a hydroxyapatite free-graft.

The device of the invention may be used in tympanic membrane or ear drum perforations involving all parts of the drum and may be used as an onlay, underlay or even inlay technique as is known in the art with existing techniques using an autograft from the subject.

Thus, the device of the present invention provides a customised graft implant for use in the repair and regeneration of a perforated tympanic membrane and/or the reconstruction and regeneration of the ear canal including the pars flaccida and scutum bone in a subject in need of such treatment. Customisation of the device can assist in facilitating regeneration of the ear drum including the tympanic membrane and/or ear canal to substantially resemble the native form thereby enabling better opportunity for improved healing and hearing outcomes for a subject. Inclusion of the fibrous middle layer in the device is particularly beneficial in making the tympanic membrane acoustically more efficient, whilst reducing the potential for atrophy, reperforation and cholesteatoma formation in the subject.

The invention also provides a method for use in the reconstruction of the ear canal including a defective pars flaccida in a subject in need of such treatment, said method comprising using the device of the invention as described herein. The pars flaccida is technically part of the ear drum, and this is the region typically involved in cholesteatoma which also erodes the adjacent bone of the ear canal called the scutum and may also involve the attic of the tympanic cavity. Thus, reconstruction of the eardrum in cholesteatoma using the device of the invention, often requires reconstruction of the attic and the scutum bone which are close and interconnected.

Thus, this treatment may be in conjunction with the repair of a tympanic membrane perforation. Alternatively, the treatment may be to reconstruct the ear canal of a subject that does not have or does not require repair of a tympanic membrane perforation.

The invention also provides for the use of a device as described herein for supporting proliferation, migration and/or adhesion of at least cells of the ear drum when grafted or implanted into the ear drum, and specifically the tympanic membrane, and/or pars flaccida or scutum bone of a subject.

In ear surgery, reconstruction of the bony ear canal following mastoidectomy is commonly required. The device may be used in the reconstruction of the scutum of a subject in need of such treatment. A benefit of using the device of the invention in this reconstruction process is that it can integrate and assist the blood supply into the area through its porous structure, and biomolecules in the device can promote growth of the subjects own cells and tissues into the reconstructed area.

In addition, the device of the invention may be used to repair or in the regeneration of the floor of the ear canal which may be diseased or damaged such as during mastoidectomy, for example, tympanomastoidectomy for chronic otitis media. In this respect, mastoid obliteration is indicated following canal wall-down tympanomastoidectomy for chronic otitis media to reduce the size of a mastoid cavity. Other indications of tympanomastoid or mastoid obliteration include reconstruction of temporal bone resection (secondary to trauma or tumour) and cerebrospinal fluid leaks. Without obliteration, a canal wall-down mastoid cavity can result in persistent otorrhea, require frequent cleaning of the cavity, difficulty with the use of a hearing aid, water immersion intolerance due to a susceptibility to infection, and propensity to vertigo. The majority of obliteration techniques consist of either local flaps (e.g. muscle, periosteum, or fascia) or free grafts (e.g. bone chips or pate, cartilage, fat, or ceramic materials such as hydroxyapatite). Whilst hydroxyapatite is the main allograft material, this needs to be covered by viable tissue in the healing phase. Allografts such as plastic mesh, Proplast and porous polypropylene had not been successful long term due to infection. Proplast was found to be associated with lasting giant cell reaction. Fistulas, persistent drainage and granulation tissue lead to gradual disuse of plastics. Finally, alloplast is devoid of cancellous bone and its stem cells and has marginal vascularity.

Thus, a device of the invention can be used in mastoid obliteration techniques for reconstruction after tympanomastoidectomy to cover a hydroxyapatite free graft.

Another benefit of the device is that it can provide rigidity and stability which, in the hostile middle ear environment found after surgery, makes it very useful in cases of cholesteatoma, atelectasis and recurrent perforations. Inclusion of polyurethane with a silk membrane will provide a longer lasting graft which can produce ongoing structural support for a patient with chronic middle ear disease such as Eustachian tube dysfunction.

EXAMPLES

Materials and Methods

Example 1—Preparation of Silk Foam

Reeled, undegummed fibres from multivoltine *Bombyx mori* silkworms were purchased from production centres in Northeast India. Fibres were degummed for 30 min at 98° C. using 2 g/L sodium carbonate (Sigma-Aldrich, St. Louis, MO, USA), and 1 g/L unscented olive oil soap (Vasse Virgin, Wilyabrup, Western Australia, Australia). Degumming was carried out using a rotary dying machine (Ahiba IR Pro, Datacolor, Lawrenceville, USA). Degummed fibres were dried overnight at 40° C. then dissolved with 9.3 M lithium bromide for 5 h at 60° C. Dissolved silk solution was dialysed at 4° C. for 3 days against deionised water (dH$_2$O) to obtain aqueous silk solution with a concentration of between 4 and 5% w/v as calculated by gravimetric analysis. The silk solution from each batch was diluted to 4% w/v, then pipetted into tubes, with 20 mL in each tube. The solution was frozen in a −80° C. freezer for 24 h. The frozen tubes were removed from the freezer, their lids removed and replaced with laboratory wipers (Kimwipes) held in place with rubber bands, then transferred to a pre-chilled FreeZone freeze-drier (Labconco, Kansas City, MO, USA) and dried for 4 days.

Example 2—Preparation of Blended Silk Fibroin/Polyurethane Membranes

Freeze-dried silk foam was sliced into small pieces with a scalpel and added to a sterile centrifuge tube together with polyurethane pellets. The two materials were then dissolved in 1,1,1,3,3,3-Hexafluoro-2-propanol (HFIP) for 5 h on a rotary mixer at room temperature. The amount of silk, polyurethane and HFIP used was calculated so that the final concentrations of the two materials were 5% (w/v) polyurethane and 1.25% (w/v) silk fibroin (or 1:4 silk:polyurethane). Dissolved samples were centrifuged at 7000×g for 2 min to remove bubbles, then cast into 55 mm diameter Petri dishes and allowed to dry for 24 h in a fume hood. The final thickness of all membranes was 100 μm.

Example 3—UV-Visible Spectrophotometry

Film transparency over the visible wavelengths was measured using a Cary 5000 UV-Visible spectrophotometer (Agilent, Santa Clara, CA, USA) with Diffuse reflectance accessory. The % transmittance of samples was determined by scanning from 700 to 380 nm. Samples were scanned with the reference standard attached to determine total transmittance and again with a light trap attached to determine the diffuse transmittance. The resulting total and diffuse transmittance scans were plotted together for each film type. The haziness of each sample was also quantified at 380, 550 and 700 nm.

Example 4—Tensile Mechanical Properties

Films for tensile testing were sliced into 5 mm wide strips, then conditioned at 20° C.±2° C. and 65%±2% relative humidity for at least 48 h prior to tensile testing. Tensile testing was conducted using a model 5967 tester (Instron, Norwood, MA, USA) with a 100 N load cell. Samples were tested until break using a gauge length of 15 mm. An extension rate of 15 mm/min and a pre-load of 0.1 N. The thickness of each film was measured before cutting into strips; films were measured in 6 places using a three-decimal-place digital micrometer (Kinchrome, Melbourne, Australia). The average thickness of these measurements was used to calculate the cross-sectional area and subsequently, the stress and strain of each film. A minimum of 20 strips were tested across at least 3 films; tensile properties were expressed as mean±standard deviation of these measurements.

Example 5—Film Acoustic Properties

Circular samples were mounted onto the end of a custom built model ear canal consisting of a hollow nylon tube with an internal diameter of 7.5 mm. An ER-2 audiology earphone (Etymotic Research, Elk Grove Village, IL, USA) mounted to the opposite end of the tube was used to excite the sample with a periodic chirp signal generated by a PCI signal generator (PCI-6711, National Instruments, Austin, USA). A probe microphone (ER-7C; Etymotic Research) was used to measure the dynamic pressure response within the canal. The probe was fed through a hole in the canal wall so that it sat immediately adjacent to the sample within the canal. The acoustic response of the different materials was determined using a laser Doppler vibrometer (CLV-2534, Polytec, Waldbronn, Germany), which was focused onto the exposed side of the clamped sample.

The signal from both the vibrometer and probe microphone were detected using a data acquisition card (PCI-4462, National Instruments) connected to a dedicated PC. A fast Fourier transfer was performed over the frequency range from 12.5 Hz to 20 kHz using the software package Vibsoft 84 version 5.0 (Polytec, Waldbronn, Germany) and the transfer function was calculated as dB rel 1 mm/s/Pa. The amplitude of the first resonance peak was calculated by first excluding all frequencies under 100 Hz and over 8 kHz. The maximum amplitude and the corresponding frequency were determined using Origin 2015. The FFT plot for each sample was displayed to confirm that this maximum related to the first resonance peak. These measurements were determined for 30 measurements per sample (10 silk membranes with three 10 mm disks punched from each membrane). The average peak frequency and amplitude were used to describe the sound transmission properties of the different materials tested.

Example 6—Lateral Displacement of Films Under Pressure Loads

To test the suitability of the silk films as a material for eardrum repair, films were tested in a custom built model ear canal designed to apply pressure of up to 7 kPa to the film. The model consisted of a nylon plastic tube with internal dimensions that match the average human ear canal as described in the literature (Grewe et al., 2013). The film disc was held against one end of the tube (to represent the middle ear side of the tube) using a screw on cap with a rubber O-ring while the other end of the tube (representing the outer opening of the ear) was connected to a syringe pump. A pressure sensor was connected via a small port within the tube immediately in front of the sample so that the pressure could be monitored in real time. A small electronic displacement sensor was placed immediately in front of the film. The optical sensor consisted of an infrared (IR) LED and detector, the distance between the sample and the sensor was measured as changes in the intensity of the reflected IR light. The sensor produced a linear variation of output voltage with distance between 2 mm to 5 mm (as measured by a linear translation stage). A small dot of white correction fluid was placed at the centre of each sample to improve its reflectance.

Example 7—Film Secondary Structure

The proportion of crystalline (β-sheet and turn) and amorphous (α-helix and random coil) motifs was measured in each film type using a Vertex 70 fourier transform infrared (FTIR) spectrophotometer (Bruker, Billerica, MA, USA). Scans were taken in absorbance mode over the range of 4000 to 600 $cm^{-1}$. Scans of a total of 3 films of each type were taken, with 6 scans taken per film (edge of the film, top surface, edge of the film bottom surface, centre of the film top surface, centre of the film bottom surface) for a total of 18 measurements per film type. The top and bottom surface scans were averaged, and the amide I region (1705 to 1595 $cm^{-1}$) was subjected to deconvolution and curve fitting using 7 known conformational positions as described previously (Rajkhowa et al., 2012). The relative peak area of each of these 7 deconvoluted peaks was used to determine the % content of side chain, β-sheet, random coil, α-helix and β-turn. The % peak area values were expressed as the mean±standard deviation of 6 measurements (centre and edge region of 3 separate films). The averaged scan of all samples per film type was also plotted after deconvolution.

Example 8—Resistance to Degradation

Films were tested using an in vitro enzymatic degradation study using a modified method based on previous work (Rajkhowa et al., 2011). Films were conditioned at 20° C.±2° C. and 65%±2% relative humidity for at least 48 h, then cut into 5 strips per film. The weight of each sample was recorded using a 4 decimal place balance before the film strips were sterilised using UV light for 30 min. Each strip was then aseptically transferred to a 15 mL plastic tube. Control samples were incubated with 0.1 M phosphate buffered saline (PBS) pH 7.4 while experimental samples were incubated with 0.1 M PBS containing 1 mg/mL Protease XIV (Sigma-Aldrich, St. Louis, MO, USA). Samples were incubated over 3 days; the protease solution and buffer was changed each day to maintain optimal enzyme activity. Samples were removed after 6 h, 1 day and 3 days. At each time point, control and experimental film strips were removed from the incubator and rinsed thoroughly with $dH_2O$, then soaked in 2% acetic acid for 30 min to remove bound protease. Strips were then thoroughly rinsed again to remove acetic acid and dried overnight in a fumehood. Once dry, the film strips were conditioned again to 20° C.±2° C. and 65%±2% relative humidity for at least 48 h and re-weighed. A total of 5 strips were weighed for each experimental group and at each time point. The weight loss of samples at each time point was presented as the mean standard deviation of the 5 samples expressed as percentage of the original (conditioned) weight.

Example 9—Surface Metrology and Roughness

The surface roughness of each sample is calculated using optical profilometry. Briefly, the top and bottom of 3 films is imaged on a Veeco Dektak 150 Contour GT (Bruker, Billerica, MA, USA). Scans are taken at a magnification of 50× using a 2× multiplier. The output file for each scan is then imported into the open source software Gwyddion (version 2.44); the scans are corrected by plane levelling, then the root mean square (RMS) roughness ($R_q$) is calculated. Any missing data identified by Gwyddion is masked and excluded from roughness calculations. Roughness data is presented as the mean±standard deviation of the 3 films of each type that were measured.

Example 10—Scanning Electron Microscopy

Samples in tissue culture plates are rinsed in PBS for 30 minutes at RT then dehydrated with increasing grades of ethyl alcohol for 1 hour each at RT (50%, 70%, 95%, 100% super dry 2 changes). Critical point drying of the samples in $CO_2$ is performed in an Emitech, model K850 critical point dryer. Sputter coating at 0.07 torr in Argon gas is performed for 2 mins at 25 kV in a Polaron Equipment Inc, model E5100 sputter coater. Samples are mounted on aluminium stubs and viewed in a Philips, model XL30 scanning electron microscope. Images are taken at 18×, 200× and 500× magnification. Image information was recorded on the data-bar that is imprinted on each image.

Example 11—Nanoindentation

Materials are superglued onto metal stubs and placed onto the stage of a Hysitron NanoIndenter 950. Samples are calibrated against an aluminium control sample. For each test sample 20 measurements are made for hardness and a reduced modulus is calculated in software at each measurement point.

Example 12—Cell Migration

Human tympanic membrane keratinocytes from stock cultures grown in DMEM/10% FBS are plated into transwell culture inserts for 24 hours. Transwell membranes should be previously perforated with 2 mm biopsy punches to create 3 holes. The inserts are placed over the test materials and cells are covered in culture medium. Over 48 hours the cells migrate from the support membrane to the test material. Cells are then fixed in formalin and the cells that have migrated onto test materials are imaged on fluorescent microscope after nuclear staining (DAPI) and mounted on slides under coverslips in PBS/glycerol polyurethane. The amount of migration is estimated based on proportion of the surface area covered.

Example 13—Cell Viability

Quantitative colorimetric assays for cell viability is performed using human tympanic membrane keratinocyte cultures with 5% DMSO as a cytotoxic control. Assays are performed using a CellTiter 96@ Aqueous One Solution Cell Proliferation Assay kit in 96 well culture plates and cell number estimated by MTS substrate conversion. Plates are read in an Epoch, BioTek plate reader.

Figure 1B:
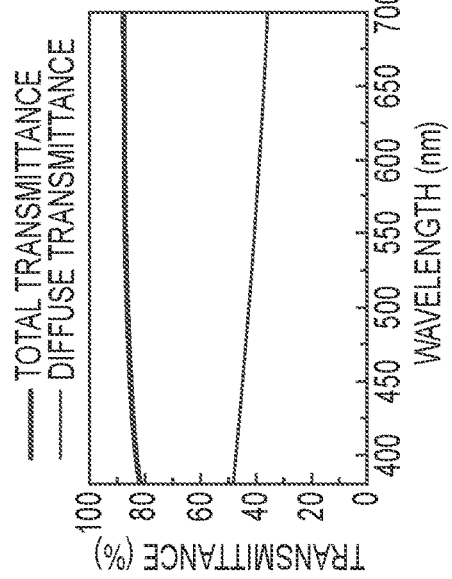
FIG. 1B is a plot showing the transparency of pure polyurethane membranes as a function of wavelength.
Figure 1C:
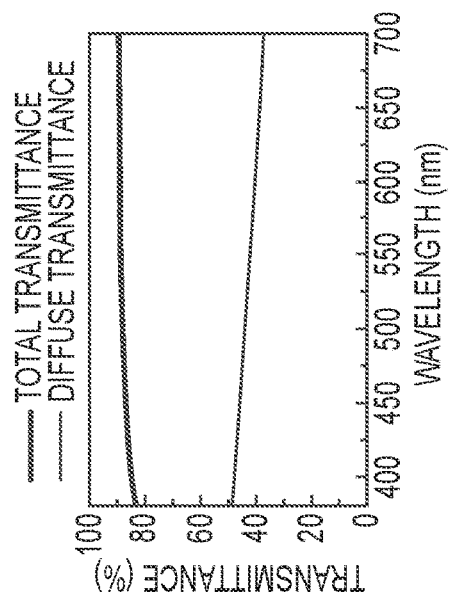
FIG. 1C is a plot showing the transparency of and 1:4 mix of silk:polyurethane membranes as a function of wavelength.

Results:

Transparency:

Polyurethane based membranes showed a similar total transparency to pure silk membranes over the visible wavelengths (FIG. 1). Polyurethane based membranes did show higher diffuse transmittance, suggesting they scatter light more (making the film slightly foggy/hazy). However, this is dependent on the type of polyurethane used. Other polyurethanes that are more or less transparent may also be selected.

Figure 2:
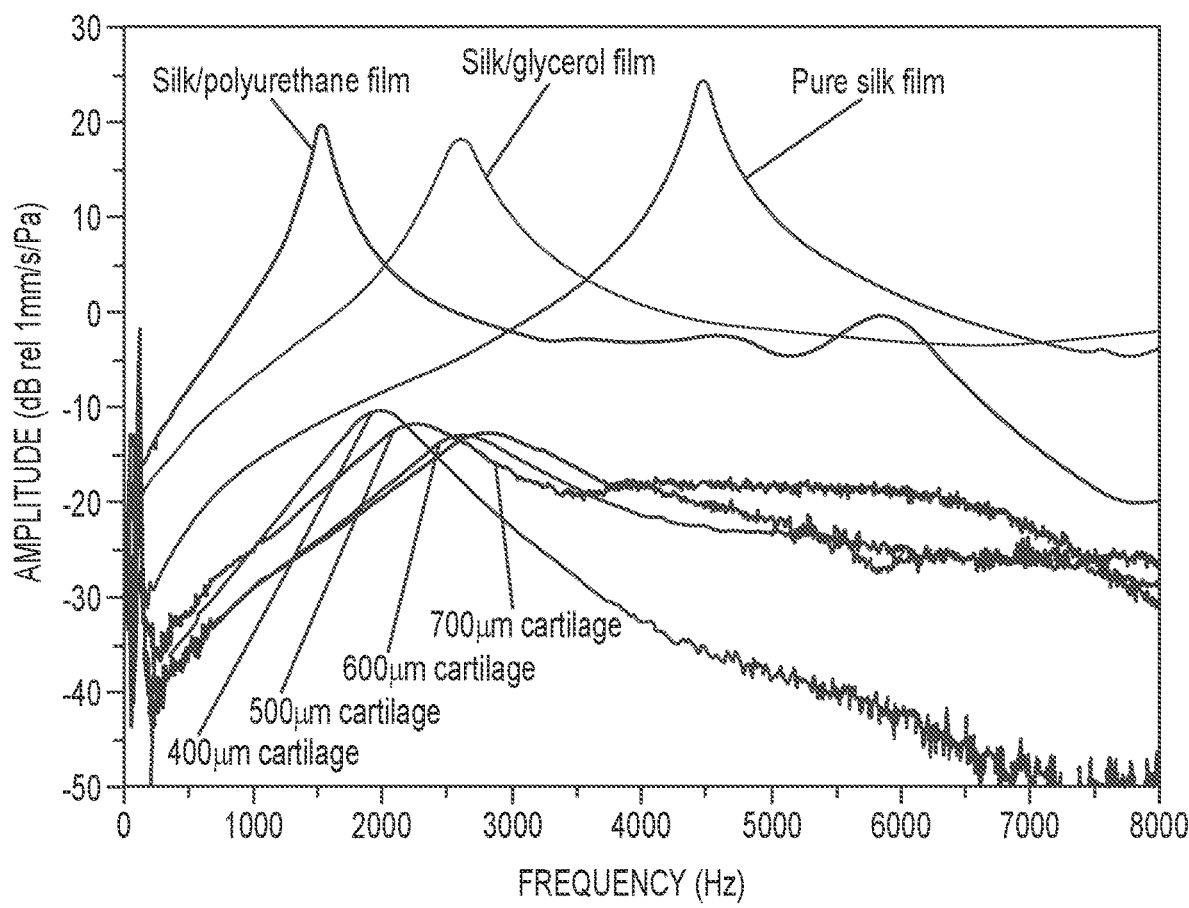
FIG. 2 is a plot showing the frequency response of 1:4 silk:polyurethane film compared with pure silk film and silk film containing 40% (w/w) glycerol.

Acoustic Properties (LDV):

The lower stiffness of the polyurethane improves the acoustic properties of silk based membranes (FIG. 2). Compared with pure silk membranes, the silk/polyurethane membranes have a lower resonance peak, bringing them closer to the resonance of the native eardrum (between 500 and 1,000 Hz). The higher amplitude of the silk based membranes is maintained; compared with pure silk membranes, vibrational amplitude is better at frequencies less than 3,000 Hz (FIG. 2).

Mechanical Properties (Tensile Strength, Young's Modulus, Maximum Elongation, Displacement Under Air Pressure Loads, Nanoindentation):

Displacement Under Air Pressure Loads:

Table 1 shows that overall the stiffness (Young's modulus) decreased and the elongation at break increased as the polyurethane content increased in the films. This is consistent with the overall feel of the films. The higher polyurethane content in the film, the more elastic and flexible it feels. It is suggested that as polyurethane becomes the predominant component (ie. when there is more than 50% polyurethane in the film), then the polyurethane becomes the matrix and the spheres of silk sit within this matrix. The silk acts as a stiffening agent.

TABLE 1

The dry mechanical properties of pure silk, silk + polyurethane blended films compared with pure silk and pure polyurethane films.

| Sample | Tensile strength (MPa) | Young's modulus (MPa) | Elongation at break (%) | Sample size (n) |
| --- | --- | --- | --- | --- |
| Pure silk (dry HFIP films, about 100 um) | 45.05 ± 4.37 | 1,875.89 ± 243.96 | 4.25 ± 1.63 | 16 |
| Silk + TPU (5:1) | 22.93 ± 2.81 | 1,336.83 ± 194.58 | 27.85 ± 13.13 | 20 |
| Silk + TPU (1:1) | 4.95 ± 0.89 | 138.58 ± 52.44 | 91.50 ± 55.50 | 17 |
| Silk + TPU (1:2) | 9.30 ± 2.88 | 78.80 ± 35.91 | 335.43 ± 99.95 | 20 |
| Pure TPU | 13.66 ± 0.65 | 8.22 ± 1.82 | 862.00 ± 108.20 | 12 |

TPU = thermoplastic polyurethane.

Chemical Properties (W-Sheet Content, Resistance to Degradation):

Resistance to Degradation

Figure 3:
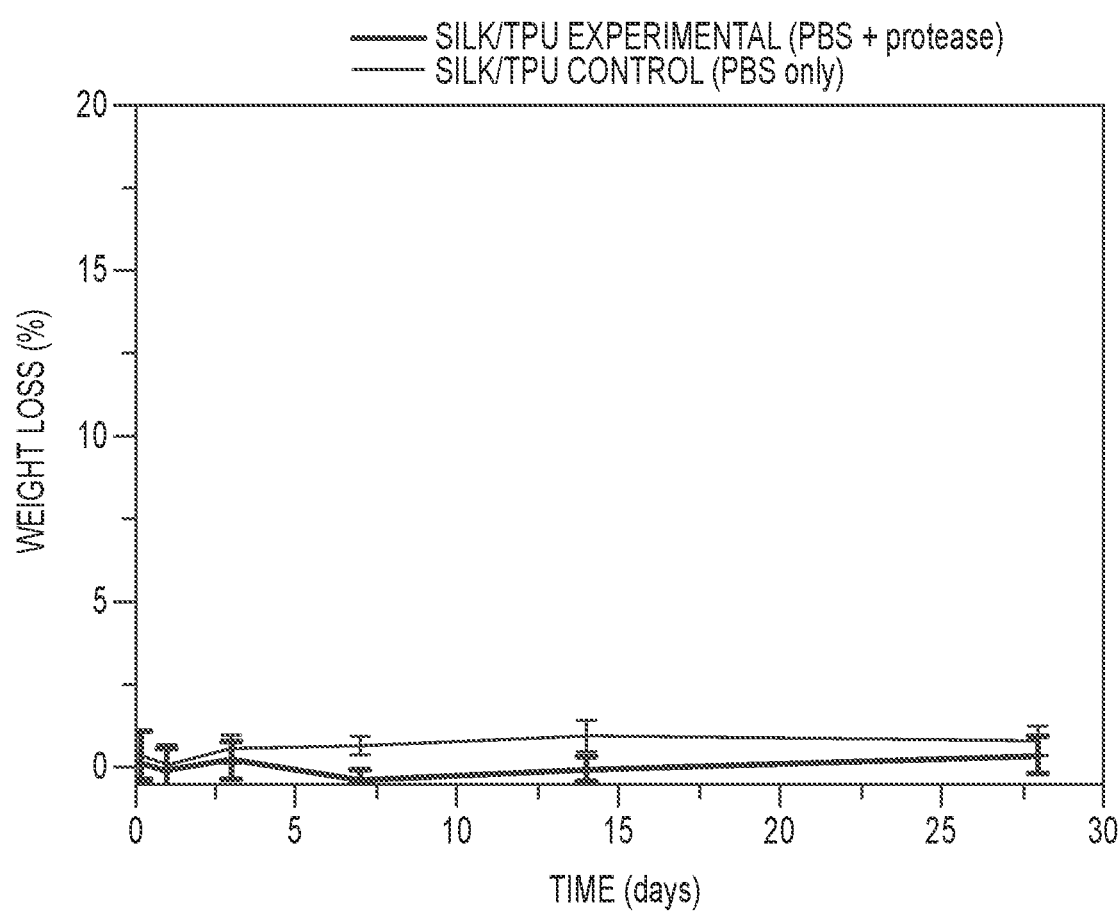
FIG. 3 is a plot showing weight loss resulting from in vitro degradation of 1:4 mix of silk/polyurethane over 28 days exposed to 1 mg/mL protease solution.

No significant degradation was detected when incubated in vitro with 1 mg/mL protease enzyme cocktail for 28 days (FIG. 3). Mean weight loss after 28 days was 0.8% w/w compared with control films (incubated without the enzyme), which lost 0.4% w/w. This was a significant improvement over silk membranes plasticized with glycerol.

The protease type used and concentration chosen were based on previous methods and chosen for their efficiency in degrading silk fibres (Horan et al., 2005). The study can be seen as an accelerated degradation study. Degradation is considered to be much slower in an in vivo environment.

REFERENCES

Grewe, J., Thiele, C., Mojallal, H., Raab, P., Sankowsky-Rothe, T., Lenarz, T., Blau, M. & Teschner, M. 2013. New HRCT-based measurement of the human outer ear canal as a basis for acoustical methods. *American Journal of Audiology.* 22, 65-73.

Horan, R. L., Antle, K., Collette, A. L., Wang, Y., Huang, J., Moreau, J. E., Volloch, V., Kaplan, D. L. & Altman, G. H. 2005. In vitro degradation of silk fibroin. *Biomaterials.* 26, 3385-3393.

Jose, R. R., Brown, J. E., Polido, K. E., Omenetto, F. G. & Kaplan, D. L. 2015. Polyol-Silk Bioink Formulations as Two-Part Room-Temperature Curable Materials for 3D Printing. *ACS Biomaterials Science & Engineering,* 1, 780-788.

Rajkhowa, R., Hu, X., Tsuzuki, T., Kaplan, D. L. & Wang, X. 2012. Structure and biodegradation mechanism of milled *Bombyx mori* silk particles. *Biomacromolecules,* 13, 2503-12.

Rajkhowa, R., Levin, B., Redmond, S. L., Li, L. H., Wang, L. J., Kanwar, J. R., Atlas, M. D. & Wang, X. G. 2011. Structure and properties of biomedical films prepared from aqueous and acidic silk fibroin solutions. *Journal of Biomedical Materials Research Part A,* 97A, 37-45.

Z. Bai, W. Xu, J. Xu, H. Yang, S. Xiao, X. Liu, et al., Fabrication and characterization of silk fibroin powder/polyurethane fibrous membrane, Polymer Engineering & Science. 52 (2012) 2025-2032. doi:10.1002/pen.23150.

X. Liu, C. Zhang, W. Xu, H. Liu, C. Ouyang, Blend films of silk fibroin and water-insoluble polyurethane prepared from an ionic liquid, Materials Letters. 65 (8) 2489-2491. doi:10.1016/j.nmatlet.2011.05.017.

X. Y. Liu, C. C. Zhang, W. L. Xu, C. Ouyang, Controlled release of heparin from blended polyurethane and silk fibroin film, Materials Letters. 63 (1) 263-265. doi: 10.1016/j.nmatlet.2008.10.006.

Y. Nakazawa, A. Asano, C. T. Nakazawa, T. Tsukatani, T. Asakura, Structural characterization of silk-polyurethane composite material for biomaterials using solid-state NMR, Polym J Polym J. 44 (2012) 802-807.

H. S. Park, M. S. Gong, J. H. Park, S. I. Moon, I. B. Wall, H. W. Kim, et al., Silk fibroin-polyurethane blends: physical properties and effect of silk fibroin content on viscoelasticity, biocompatibility and myoblast differentiation, Acta Biomaterialia. 9 (2013) 8962-71. doi:10.1016/j.actbio.2013.07.013.

Um, In-Chul, Hae-Yong Kweon, Chang mo Hwang, Byung-Goo Min, and Young-Hwan Park. 'Structural Characteristics and Properties of Silk Fibroin/Polyurethane Blend Films'. International Journal of Industrial Entomology 5, no. 2 (2002): 163-70.

P. Petrini, C. Parolari, M. C. Tanzi, Silk fibroin-polyurethane scaffolds for tissue engineering, Journal of Materials Science: Materials in Medicine. 12 (2001) 849-853. doi: 10.1023/A:1012847301850.

T. Yongzhen, Y. Yun, X. Weilin, Z. Wenhui, Preparation, structure and properties of blended films of polyurethane and silk fibroin, Acta Polymerica Sinica. 1 (2010) 27-32. doi:10.3724/sp.j.1105.2010.00027.

M. Zhou, W. C. Wang, Y. G. Liao, W. Q. Liu, M. Yu, C. X. Ouyang, In vitro biocompatibility evaluation of silk-fibroin/polyurethane membrane with cultivation of HUVECs, Front. Mater. Sci. (2014) 1-9. doi:10.1007/s11706-014-0230-3.

WO2012090553A1

What is claimed is:

1. A method of making a blended silk fibroin polyurethane membrane matrix, the method consisting of the steps of:
   a. dissolving dried, degummed silk fibers in a chaotropic salt or a chaotropic salt solution to form a silk fiber solution, wherein the chaotropic salt is selected from lithium bromide, lithium chloride, zinc chloride, calcium chloride, lithium thiocyanide, and aqueous ethanol solutions thereof;
   b. freezing the silk fiber solution to form a frozen silk fiber solution;
   c. freeze-drying the frozen silk fiber solution to form a silk foam;
   d. dissolving the silk foam in formic acid to form an acidic silk solution;
   e. mixing the acidic silk solution with a biocompatible polyurethane to form a silk/polyurethane mixture;
   f. adding a solvent to the silk/polyurethane mixture to form a dissolved silk/polyurethane mixture;
   g. casting the dissolved silk/polyurethane mixture into a mold; and
   h. drying the dissolved silk/polyurethane mixture in the mold to form a blended silk fibroin polyurethane membrane matrix.

2. The method of claim 1 wherein the chaotropic salt is lithium bromide.

3. The method of claim 1 wherein the freezing comprises storing at −80° C.

4. The method of claim 1 wherein the solvent comprises an alcohol.

5. The method of claim 1 wherein the silk fibroin polyurethane membrane matrix comprises at least 90% w/v of the biocompatible polyurethane.

* * * * *